United States Patent
Allen et al.

(10) Patent No.: US 8,143,479 B2
(45) Date of Patent: Mar. 27, 2012

(54) PLASTIDIC PHOSPHOGLUCOMUTASE GENES

(75) Inventors: Stephen M. Allen, Wilmington, DE (US); Thomas J. Carlson, San Diego, CA (US); William D. Hitz, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 1145 days.

(21) Appl. No.: 11/773,013

(22) Filed: Jul. 3, 2007

(65) Prior Publication Data

US 2009/0013432 A1 Jan. 8, 2009

Related U.S. Application Data

(62) Division of application No. 09/906,209, filed on Jul. 16, 2001, now Pat. No. 7,250,557.

(60) Provisional application No. 60/218,712, filed on Jul. 17, 2000.

(51) Int. Cl.
  C12N 15/82 (2006.01)
  C12N 15/63 (2006.01)
  C12N 15/10 (2006.01)
  C07H 21/04 (2006.01)
  A01H 5/00 (2006.01)
  A01H 5/10 (2006.01)

(52) U.S. Cl. ..... 800/284; 800/278; 800/295; 435/320.1; 435/468; 536/23.1; 536/23.6

(58) Field of Classification Search .................. None
  See application file for complete search history.

(56) References Cited

U.S. PATENT DOCUMENTS

| | | | |
|---|---|---|---|
| 5,846,784 A | 12/1998 | Hitz | |
| 6,538,180 B1 * | 3/2003 | Lacey et al. | 800/284 |
| 2002/0165385 A1 * | 11/2002 | Allen et al. | 536/23.6 |
| 2004/0034888 A1 * | 2/2004 | Liu et al. | 800/289 |

FOREIGN PATENT DOCUMENTS

| | | |
|---|---|---|
| EP | 1001029 A1 | 5/2000 |
| WO | 9411516 A1 | 5/1994 |
| WO | 9801574 A1 | 1/1998 |
| WO | 9936551 A1 | 7/1999 |
| WO | 0011176 A2 | 3/2000 |

OTHER PUBLICATIONS

Proceedings Soybean Utilization Alternatives, University of Minnesota, Craig Coon et al., pp. 203-211, 1988, The Effect of Oligosaccharides on the Nutritive Value of Soybean Meal.
National Center for Biotechnology Information General Identifier No. 6272125, Nov. 4, 1999, C. J. Harrison et al., The RUG3 Locus of Pea Encodes Plastidial Phosphoglucomutase.
National Center for Biotechnology Information General Identifier No. 6272283, Nov. 4, 1999, C. J. Harrison et al., The RUG3 Locus of Pea Encodes Plastidial Phosphoglucomutase.
National Center for Biotechnology Information General Identifier No. 10190529, Sep. 16, 2000, C. J. Harrison et al., Method for Increasing Sucrose Content of Plants.
T. M. Klein et al., Nature, vol. 327:70-73, 1987, High-Velocity Microprojectiles for Delivering Nucleic Acids Into Living Cells.
EMBL Sequence Database Library Accession No. AW781992, May 14, 2000, R. Shoemaker et al., Public Soybean EST Project.
EMBL Sequence Database Library Accession No. AC002311, Jul. 10, 1997, N. A. Federspiel et al.
EMBL Sequence Database Library Accession No. AI416493, Feb. 11, 1999, R. Shoemaker et al., Public Soybean EST Project.
EMBL Sequence Database Library Accession No. U84888, Feb. 8, 1997, C.B. Michalowski et al., Mesembryanthemum Crystallinum Phosphoglucomutase mRNA.

* cited by examiner

Primary Examiner — Brent T Page

(57) ABSTRACT

This invention relates to an isolated nucleic acid fragment encoding a plastidic phosphoglucomutase protein. The invention also relates to the construction of a chimeric gene encoding all or a substantial portion of the plastidic phosphoglucomutase, in sense or antisense orientation, wherein expression of the chimeric gene results in production of altered levels of the plastidic phosphoglucomutase in a transformed host cell.

15 Claims, 4 Drawing Sheets

FIG. 1A

```
SEQ ID NO: 12    1  MAF------CY-RLDN-FIISAFKPKHSNVPLSI-----------HHSS--SNFPSFKVQNFPFR
SEQ ID NO: 13    1  MAF------CY-RLDN-FIISAFKPKHSNVPLSI-----------HHSS--SNFPSFKVQNFPFR
SEQ ID NO: 08    1  MAF------SC-KLDS-FILSAYKPQNSILPLSI-----------QPSSFLPSPSSLKPQKLPFR
SEQ ID NO: 04    1  M--------------------------------PTM---------------------HALRLCPLL--
SEQ ID NO: 10    1  TRLARFLPRCKRNTTSPHSPSRLFSPSPPPLLSAWRWHCRPPHRLGMASHALRLHPLLFS
SEQ ID NO: 02    1  AP-ARY-----RHLSLSQSLSPYL---------------------QEMAMSVPTMRLHPLVPS
SEQ ID NO: 11    1  MSS------TYARFDTVFLLSRF-AGAKYSPLWP-----------SSSS--SSHSSLLSSGIHLR
                                                                                   60

*    *****
SEQ ID NO: 12   45  VRYNSAIRATSSSSSTPTT--IA-----------------------EPNDIKINSIPTKPIEGQ
SEQ ID NO: 13   45  VRYNSAIRATSSSSSTPTT--IA-----------------------EPNDIKINSIPTKPIEGQ
SEQ ID NO: 08   47  IRYGSTIRATSSSSTPSAT--IA-----------------------EPEGIKIKSIPTKPIDGQ
SEQ ID NO: 04   14  -STIRSTP---PRATAAARQ------G---AL-FVARCSSAGTPSAAQALKISSIPTKPVEGQ
SEQ ID NO: 10   61  AAAAARPAPLAARPGGGARR---VHRRHSL-AVVRCSS----SAAQALKIKSIPTKPVEGQ
SEQ ID NO: 02   37  SKLLSPSSSPAVLVSSRIPLLSLRRPNLRFSVKATASSTPSTAESIKIKSIPTKPVEGQ
SEQ ID NO: 11   46  AKPNSRLRSVTGASSSSSGPIIA-----------------------GSESIEIKSLPTKPIEGQ
                                                                                  120

*********** *  * *********************   *  * ***  *
SEQ ID NO: 12   84  KTGTSGLRKKVKVFKQENYLANWIQALFNSLPPEDYKNGLLIVLGGDGRYFNKEAAQIIIK
SEQ ID NO: 13   84  KTGTSGLRKKVKVFKQENYLANWIQALFNSLPPEDYKNGLLIVLGGDGRYFNKEAAQIIIK
SEQ ID NO: 08   86  KTGTSGLRKKVKVFMQDNYLANWIQALFNSLPPEDYKNGLLIVLGGDGRYFNKEAAQIIIK
SEQ ID NO: 04   63  KTGTSGLRKKVKVFQQENYLANWIQALFNSLPPEDYKNGLLIVLGGDGRYFNQEAAQIIIK
SEQ ID NO: 10  113  KTGTSGLRKKVKVFQQENYLANWIQALFNSLPPEDYVGATLVLGGDGRYFNKEAAQIIIK
SEQ ID NO: 02   97  KTGTSGLRKKVKVFQQENYLANWIQALFNSLPPEDYVGGTLVLGGDGRYFNKDAAQIITK
SEQ ID NO: 11   87  KTGTSGLRKKVKVFMQDNYLANWIQALFNSLPLEDYKDATIVLGGDGRYFNKEASQIIIK
                                                                                  180
```

FIG. 1B

```
                          *       **  ***    * *  ********  *   *****************       ******
SEQ ID NO: 12    144   IAAGNGVGKILVGKEGILSTPAVSAVIRKREANGGFIMSASHNPGGPEYDWGIKFNYSSG
SEQ ID NO: 13    144   IAAGNGVGKILVGKEGILSTPAVSAVIRKREANGGFIMSASHNPGGPEYDWGIKFNYSSG
SEQ ID NO: 08    146   IAAGNGVGKILVGKEGILSTPAVSAVIRKKRKANGGFIMSASHNPGGPEYDWGIKFNYSSG
SEQ ID NO: 04    123   IAAGNGVQKIIVGRNGLLSTPAVSAVIRKKRKANGGFIMSASHNPGGPDNDWGIKFNYSSG
SEQ ID NO: 10    173   IAAGNGVGKILVGRNGLLSTPAVSAVIRKRQANGGFIMSASHNPGGPDYDWGIKFNYSSG
SEQ ID NO: 02    157   IAAGNGVGKILVGRDGIMSTPAVSAVIRKQKANGGFIMSASHNPGGPDYDWGIKFNYSSG
SEQ ID NO: 11    147   IAAGNGVGKILVGQEGILSTPAVSAVIRKRKANGGFIMSASHNPGGPEYDWGIKFNYSSG
                                                                                    240

******  ***  **   *  **  *  *   **  *  *      **  ****** *
SEQ ID NO: 12    204   QPAPESITDKIYGNTLSISEIKIADIPDVDLSNVGVTKFGSFSVEVIDPVSDYLELLETV
SEQ ID NO: 13    204   QPAPESITDKIYGNTLSISEIKIADIPDVDLSNVGVTKFGSFSVEVIDPVSDYLELLETV
SEQ ID NO: 08    206   QPAPESITDKIYGNTLSISEIKIADIPDVDLSKVGVTNFGSFSVEVIDPVSDYLELLETV
SEQ ID NO: 04    183   QPAPETITDQIYGNTLSISEIKTADIPDTDLSSVGVVSYGDFAIEVIDPVSDYLELMENV
SEQ ID NO: 10    233   QPAPETITDQIYGNTLSISEIKTADIPDVDLSSLGVVSYGDFTVEVIDPVLDYLELMENV
SEQ ID NO: 02    217   QPAPESITDKIYGNTLSISEIKISDIPDIDLSSLGVTNYGNFSVEVVDPVSDYLELMENV
SEQ ID NO: 11    207   QPAPESITDKIYGNTLSISEIKVAEIPDIDLSHVGVTKYGNFSVEVIDPISDYLELMEDV
                                                                                    300

***  **    *    *   ****   ** *            ** *******  ****
SEQ ID NO: 12    264   FDFQLIKSLISRPDFRFTFDAMHAVAGAYATPIFVDKLSASLDSISNGIPLEDFGHGHPD
SEQ ID NO: 13    264   FDFQLIKSLISRPDFRFTFDAMHAVAGAYATPIFVDKLGASPDSISNGIPLEDFGHGHPD
SEQ ID NO: 08    266   FDFQLIRGLLSRPDFRFIFDAMHAVTGAYAKPIFVDKLGASLDSISNGIPLEDFGNGHPD
SEQ ID NO: 04    243   FDFQLIKDLLSRPDFRFIFDAMHAITGAYAGPIFVEKLGADPDCILNGVPLEDFGNGHPD
SEQ ID NO: 10    293   FDFQLIKGLLSRPDFRFVFDAMHAVTGAYADPIFVEKLGADPDYILNGVPLEDFGNGHPD
SEQ ID NO: 02    277   FDFQLIKGLLSRSDFRFTFDAMHAVTGAYAKPIFVERLRASPDCVLNGVPLEDFGHGHPD
SEQ ID NO: 11    267   FDFDLIRGLLSRSDFGMFDAMHAVTGAYAKPIFVDNLEAKPDSISNGVPLEDFGHGHPD
                                                                                    360
```

FIG. 1C

```
                            *******  **       *  **  **********************  **  ******  ****
SEQ ID NO: 12    324    PNLTYAKDLVKIMYAENGPDFGAASDGDGDRNMILGTSFFVTPSDSVAVIAANAKEAIPY
SEQ ID NO: 13    324    PNLTYAKDLVNIMYAENGPDFGAASDGDGDRNMILGTSFFVTPSDSVAVIAANAKEAIPY
SEQ ID NO: 08    326    PNLTYAKDLVDILYAENGPDFGAASDGDGDRNMILGRSFFVTPSDSVAVIAANAREAIPY
SEQ ID NO: 04    303    PNLTYAKELVFTMFGTHAPDFGAASDGDGDRNMILGKRFFITPSDSVAIIAANAQTAIPY
SEQ ID NO: 10    353    PNLTYAKELVFTMFGSGAPDFGAASDGDGDRNMILGRRFFVTPSDSVAIIAANAQAAIPY
SEQ ID NO: 02    337    PNLTYAKELVDVMYTTDAPDLGAASDGDGDRNMILGRRFFVTPSDSVAMIAANAQAAIPY
SEQ ID NO: 11    327    PNLTYAKDLVDVMYRDDGPDFGAASDGDGDRNMVLGNKFFVTPSDSVAIIAANAQEAIPY
                        361                                                           420

*********  ****  *  *  **************************  *********
SEQ ID NO: 12    384    FKDSIKGLARSMPTSGALDRVAEKLNLPFFEVPTGWKFFGNLMDAGNLSICGEESFGTGS
SEQ ID NO: 13    384    FKDSIKGLARSMPTSGALDRVAEKLNLPFFEVPTGWKFFGNLMDAGNLSICGEESFGTGS
SEQ ID NO: 08    386    FKNGVKGLARSMPPSGALDRVAKKLNLPFFEVPTGWKFFGNLMDAGNLSVCGEESFGTGS
SEQ ID NO: 04    363    FQFGTKGLARSMPTSGALDRVAEKLNVPFFEVPTGWKFFGNLMDAGKLSICGEESFGTGS
SEQ ID NO: 10    413    FQSGPKGLARSMPTSGALDRVADKLNVPFFEVPTGWKFFGNLMDAGKLSICGEESFGTGS
SEQ ID NO: 02    397    FQAGPKGLARSMPTSGALDRVAEKLNLPFFEVPTGWKFFGNLMDAGKLSICGEESFGTGS
SEQ ID NO: 11    387    FRAGPKGLARSMPTSGALDRVAEKLKLPFFEVPTGWKFFGNLMDAGKLSICGEESFGTGS
                        421                                                           480

**********************  *  *      *   *  *       **************
SEQ ID NO: 12    444    DHIREKDGIWAVLAWLSIIAHRNKDTKPGEKLVSVSDVVKEHWATYGRNFFSRYDYEECE
SEQ ID NO: 13    444    DHIREKDGIWAVLAWLSIIAHRNKDTKPGEKLVSVSDVVKEHWATYGRNFFSRYDYEECE
SEQ ID NO: 08    446    DHIREKDGIWAVLAWLSIIAHRNKDKNPGEKLISVSDVVMEHWATYGRNFFSRYDYEACE
SEQ ID NO: 04    423    DHIREKDGIWAVLAWLSIIAHRNKDKKVGERLVSVEDIAMEHWKTYGRNFFSRYDYEECE
SEQ ID NO: 10    473    DHIREKDGIWAVLAWLSILAHRNKDKKAGERLVSVEDVAREHWATYGRNFFSRYDYEECE
SEQ ID NO: 02    457    DHIREKDGIWAVLAWLSIIAYRNKDKKIGEKLVSVEDIAKEHWAKYGRNFFSRYDYEECE
SEQ ID NO: 11    447    DHIREKDGIWAVLAWLSILAHRIKDKKPGEKLVSVADVVNEYWATYGRNFFSRYDYEECE
                        481                                                           540
```

FIG. 1D

```
                          *   *** ***  **  *        *     *     ***** ***********
SEQ ID NO: 12    504      SEGANKMIEYLRELLSKSKPGDKYGSYVLQFADDFTYTDPVDGSVVSKQGVRFVFTDGSR
SEQ ID NO: 13    504      SEGANKMIEYLRELLSKSKPGDKYGSYVLQFADDFTYTDPVDGSVVSKQGVRFVFTDGSR
SEQ ID NO: 08    506      SEGANKMIEYLRDILSKSKPGDQYGSYVLQFADDFTYTDPVDGSVVSKQGVRFVFTDGSR
SEQ ID NO: 04    483      SHSANQMMDHLRDVMANSKPGEKYGNYTLQFADDFSYTDPVDGSTVSKQGLRFVFTDGSR
SEQ ID NO: 10    533      SESANKMMEHLRDVIAKSKPGEKYGNYTLQFADDFSYTDPVDGSTVSKQGLRFVFTDGSR
SEQ ID NO: 02    517      SEGANKMMQHLRDFISTSKPGEQYGNYTLQFSDDFSYTDPVDGSVASKQGLRFVFTDGSR
SEQ ID NO: 11    507      SEGANKMIEYLRDIVAKSKAGENYGNYVLQFADDFSYKDPVDGSVASKQGVRFVFTDGSR
                          541                                                       600

*  ****  ******    *   ***   **    *  ***** ***  *****
SEQ ID NO: 12    564      IIYRLSGTGSAGATVRVYIEQFEPDVSKHDVDAQIALKPLIDLALSVSKLKDFTGREKPT
SEQ ID NO: 13    564      IIYRLSGTGSAGATVRVYIEQFEPDVSKHDVDAQIALKPLIDLALSVSKLKDFTGREKPT
SEQ ID NO: 08    566      IIYRLSGTGSAGATVRVYIEQFEPDVSKHDVDAQIALKPLIDLAISVSKLKDFTGREKPT
SEQ ID NO: 04    543      IIFRLSGTGSAGATIRLYIEQFESDISKHSLDAQTALKPLIDLALSVSKLKDFTGREKPT
SEQ ID NO: 10    593      IIFRLSGTGSAGATIRIYIEQFESDASKHDLDAQIALKPLIDLALSVSKLKDFTGRDKPT
SEQ ID NO: 02    577      VIYRLSGTGSAGATIRIYVEQFEPDVSKHDVDAQAALKPLIDLALSISKLKEFTGREKPT
SEQ ID NO: 11    567      IIYRLSGNGSAGATVRIYIEQFEPDVSKHDVDAQIAIKPLIDLALSVSKLKEFTGREKPT
                          601                                                       660

***
SEQ ID NO: 12    624      VIT
SEQ ID NO: 13    624      VIT
SEQ ID NO: 08    626      VIT
SEQ ID NO: 04    603      VIT
SEQ ID NO: 10    653      VIT
SEQ ID NO: 02    637      VIT
SEQ ID NO: 11    627      VIT
                          661 663
```

PLASTIDIC PHOSPHOGLUCOMUTASE GENES

This application is a divisional of U.S. patent application Ser. No. 09/906,209, filed Jul. 16, 2001, now U.S. Pat. No. 7,250,557, issued Jul. 31, 2007, which claims the benefit of U.S. Provisional Application No. 60/218,712, filed Jul. 17, 2000, the entire contents of each are herein incorporated by reference.

FIELD OF THE INVENTION

This invention is in the field of plant molecular biology. More specifically, this invention pertains to nucleic acid fragments encoding plastidic phosphoglucomutase proteins in plants and seeds.

BACKGROUND OF THE INVENTION

Starch synthesis occurs in the chloroplast while soluble carbohydrate (i.e., sucrose) synthesis occurs in the cytosol. These biosynthetic pathways are competing processes because excess triose phosphate can be used for either starch synthesis in the chloroplast or sucrose synthesis in the cytosol. These pathways have many common steps, however, the enzymes that catalyze similar steps are unique to each compartment. These enzymes are isozymes; different forms of the enzymes that catalyze the same reaction. For example, the plastidic and cytosolic forms of phosphoglucomutase both catalyze the conversion of glucose-6-phosphate to glucose 1-phosphate in different subcellular locations.

At maturity, about 40% of soybean seed dry weight is protein and 20% extractable oil. These constitute the economically valuable products of the soybean crop. Of the remaining 40% of seed weight, about 10% is soluble carbohydrate. The soluble carbohydrate portion contributes little to the economic value of soybean seeds and the main component of the soluble carbohydrate fraction, raffinosaccharides, are deleterious both to processing and to the food value of soybean meal in monogastric animals (Coon et al., (1988) Proceedings Soybean Utilization Alternatives, Univ. of Minnesota, pp. 203-211).

It may be possible to modulate the size of the starch and soluble carbohydrate pools in plant cells by altering the catalytic activity of specific enzymes (i.e., phosphoglucomutase) in the starch and soluble carbohydrate biosynthetic pathways (Taiz L., et al. *Plant Physiology*; The Benjamin/Cummings Publishing Company: New York, 1991). For example, during soybean seed maturation a large portion of the glucose which is converted to soluble carbohydrates (sucrose, raffinose and stachyose) during soybean seed maturation comes from the break down of a starch pool which was produced slowly during the primary growth phase. Elimination of this transient starch pool may be a strategy for diverting carbon away from the soluble carbohydrate components of dry soybean seeds (sucrose, raffinose and stachyose) and into the more economically desirable components such as oil and protein. This strategy may also be applicable to other plants such as corn, rice and wheat.

There is a great deal of interest in identifying the genes that encode proteins involved in starch and soluble carbohydrate biosynthesis in plants. The genes that code for these enzymes may be used to study the interactions among individuals of the pathways and develop methods to alter starch and soluble carbohydrate biosynthesis. Accordingly, the availability of nucleic acid sequences encoding all or a substantial portion of a plastidic or cytosolic phosphoglucomutase enzyme would facilitate studies to better understand starch and soluble carbohydrate biosynthesis in plants and provide genetic tools to enhance or otherwise alter starch and soluble carbohydrate biosynthesis.

The rug3 locus of *Pisum sativum* encodes the pea plastidic phosphoglucomutase (EP 1001029A1, the entire contents of which are herein incorporated by reference). Pea seeds, of the rug3rug3 genotype, substantially lacking plastidic phosphoglucomutase activity, have higher levels of sucrose at the end of the vining period (EP 1001029A1). High-sucrose soybean lines are known to have better industrial processing and food flavor qualities, in the production of soy protein. Consequently, decreasing or eliminating expression of the plastidic phosphoglucomutase gene in soybeans would be desirable for industrial preparation of soy protein.

SUMMARY OF THE INVENTION

The present invention concerns an isolated polynucleotide comprising: (a) a first nucleotide sequence encoding a first polypeptide comprising at least 560 amino acids, wherein the amino acid sequence of the first polypeptide and the amino acid sequence of SEQ ID NO:8 have at least 95% identity based on the Clustal alignment method, (b) a second nucleotide sequence encoding a second polypeptide comprising at least 560 amino acids, wherein the amino acid sequence of the second polypeptide and the amino acid sequence of SEQ ID NO:2, SEQ ID NO:4, or SEQ ID NO:10 have at least 85%, 90%, or 95% identity based on the Clustal alignment method, or (c) the complement of the first or second nucleotide sequence, wherein the complement and the first or second nucleotide sequence contain the same number of nucleotides and are 100% complementary. The first polypeptide preferably comprises the amino acid sequence of SEQ ID NO:8, and the second polypeptide preferably comprises the amino acid sequence of SEQ ID NO:2, SEQ ID NO:4, or SEQ ID NO:10. The first nucleotide sequence preferably comprises the nucleotide sequence of SEQ ID NO:7, the second nucleotide sequence preferably comprises the nucleotide sequence of SEQ ID NO:1, SEQ ID NO:3, or SEQ ID NO:9. The first and second polypeptides preferably are phosphoglucomutase.

In a second embodiment, the present invention relates to a chimeric gene comprising any of the isolated polynucleotides of the present invention operably linked to a regulatory sequence, and a cell, a plant, and a seed comprising the chimeric gene.

In a third embodiment, the present invention relates to a vector comprising any of the isolated polynucleotides of the present invention.

In a fourth embodiment, the present invention relates to an isolated polynucleotide fragment comprising a nucleotide sequence comprised by any of the polynucleotides of the present invention, wherein the nucleotide sequence contains at least 30, 40, or 60 nucleotides.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention relates to a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In a seventh embodiment, the present invention concerns an isolated polypeptide comprising: (a) a first amino acid sequence comprising at least 560 amino acids, wherein the first amino acid sequence and the amino acid sequence of SEQ ID NO:8 have at least 95% identity based on the Clustal alignment method, and (b) a second amino acid sequence comprising at least 560 amino acids, wherein the second amino acid sequence and the amino acid sequence of SEQ ID NO:2, SEQ ID NO:4, or SEQ ID NO:10 have at least 85%, 90%, or 95% identity based on the Clustal alignment method. The first amino acid sequence preferably comprises the amino acid sequence of SEQ ID NO:8, and the second amino acid sequence preferably comprises the amino acid sequence SEQ ID NO:2, SEQ ID NO:4, or SEQ ID NO:10. The polypeptide preferably is a phosphoglucomutase.

In an eighth embodiment, the present invention relates to a virus, preferably a baculovirus, comprising any of the isolated polynucleotides of the present invention or any of the chimeric genes of the present invention.

In a ninth embodiment, the invention relates to a method of selecting an isolated polynucleotide that affects the level of expression of a phosphoglucomutase protein or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the phosphoglucomutase protein or enzyme activity in the host cell containing the isolated polynucleotide; and (d) comparing the level of the phosphoglucomutase protein or enzyme activity in the host cell containing the isolated polynucleotide with the level of the phosphoglucomutase protein or enzyme activity in the host cell that does not contain the isolated polynucleotide.

In a tenth embodiment, the invention concerns a method of obtaining a nucleic acid fragment encoding a substantial portion of a phosphoglucomutase protein, preferably a plant phosphoglucomutase protein, comprising the steps of: synthesizing an oligonucleotide primer comprising a nucleotide sequence of at least 30 contiguous nucleotides, preferably at least 40 contiguous nucleotides, most preferably at least 60 contiguous nucleotides derived from a nucleotide sequence selected from the group consisting of SEQ ID NOs:1, 3, 5, 7, and 9, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a phosphoglucomutase protein amino acid sequence.

In an eleventh embodiment, this invention relates to a method of obtaining a nucleic acid fragment encoding all or a substantial portion of the amino acid sequence encoding a phosphoglucomutase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the phosphoglucomutase polynucleotide in an amount sufficient to complement a null mutant to provide a positive selection means.

In a thirteenth embodiment, this invention relates to a method of altering the level of expression of a phosphoglucomutase protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the phosphoglucomutase protein in the transformed host cell.

In a fourteenth embodiment, this invention relates to a method for suppressing in a plant the level of expression of a gene encoding a polypeptide having plastidic phosphoglucomutase activity, wherein the method comprises transforming a plant with the fragment of the fourth embodiment.

BRIEF DESCRIPTION OF THE DRAWING AND SEQUENCE LISTING

The invention can be more fully understood from the following detailed description and the accompanying Drawing and Sequence Listing which form a part of this application.

FIGS. 1A, 1B, 1C and 1D show an alignment of the amino acid sequences of plastidic phosphoglucomutase encoded by the nucleotide sequences derived from the following: cattail clone etrlc.pk005.f8 (SEQ ID NO:2); corn contig (SEQ ID NO:4) composed of p0075.cslaf22f (EST), p0075.cslaf22rb (EST), and p0128.cpicz81r (EST); soybean contig (SEQ ID NO:8) composed of clone sdp3c.pk003.e22 and PCR fragments; rice clone rdilc.pk001.a22 (SEQ ID NO:10); plastidic phosphoglucomutase from *Brassica napus* (NCBI Identifier No. gi 6272125; SEQ ID NO:11); plastidic phosphoglucomutase from *Pisum sativum* (NCBI Identifier No. gi 6272283; SEQ ID NO:12); and plastidic phosphoglucomutase from *Pisum sativum* described in European Patent Application EP 1001029-A (NCBI Identifier No. gi 10190529; SEQ ID NO:13). For the consensus alignment, amino acids which are conserved among all sequences at a given position, and which are contained in at least two sequences, are indicated with an asterisk (*). Dashes are used by the program to maximize alignment of the sequences. Amino acid positions for a given SEQ ID NO are given to the left of the corresponding line of sequence. Amino acid positions for the consensus alignment are given below each section of sequence.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire or functional protein derived from an FIS, a contig, an EST and PCR, or an FIS and PCR ("CGS"). Nucleotide SEQ ID NOs:1, 3, 5, and 7 correspond to nucleotide SEQ ID NOs:1, 3, 5, and 7, respectively, presented in U.S. Provisional Application No. 60/218,712, filed Jul. 17, 2000. Amino acid SEQ ID NOs:2, 4, 6, and 8 correspond to amino acid SEQ ID NOs:2, 4, 6, and 8, respectively, presented in U.S. Provisional Application No. 60/218,712, filed Jul. 17, 2000. The sequence descriptions and Sequence Listing attached hereto comply with the rules governing nucleotide and/or amino acid sequence disclosures in patent applications as set forth in 37 C.F.R. §1.821-1.825.

TABLE 1

Plastidic Phosphoglucomutase Proteins

| Protein (Plant Source) | Clone Designation | Status | SEQ ID NO: (Nucleotide) | SEQ ID NO: (Amino Acid) |
|---|---|---|---|---|
| Plastidic Phosphoglucomutase (Cattail) | etr1c.pk005.f8 (FIS) | CGS | 1 | 2 |
| Plastidic Phosphoglucomutase (Corn) | Contig Composed of: p0075.cslaf22f (EST); p0075.cslaf22rb (EST); p0128.cpicz81r (EST) | CGS | 3 | 4 |
| Plastidic Phosphoglucomutase (Rice) | rth1c.pk009.k14.f (EST) | EST | 5 | 6 |
| Plastidic Phosphoglucomutase (Soybean) | Contig Composed of: sdp3c.pk003.e22 (EST); PCR Fragments | CGS | 7 | 8 |
| Plastidic Phosphoglucomutase (Rice) | rdi1c.pk001.a22 (FIS) | CGS | 9 | 10 |

SEQ ID NO:10 corresponds to a direct translation of the nucleotide sequence for the full insert of rice clone rdi1c.pk00.a22. The amino acid sequence in SEQ ID NO:10 includes a 46 amino acid open-reading frame directly in front of, and in frame with, the methionine start codon.

SEQ ID NO:11 corresponds to plastidic phosphoglucomutase from *Brassica napus* (NCBI Identifier No. gi 6272125).

SEQ ID NO:12 corresponds to plastidic phosphoglucomutase from *Pisum sativum* (NCBI Identifier No. gi 6272283).

SEQ ID NO:13 corresponds to and plastidic phosphoglucomutase from *Pisum sativum* described in European Patent Application EP 1001029-A (NCBI Identifier No. gi 10190529).

SEQ ID NO:14 corresponds to a 574 nucleotide NotI fragment from plasmid pTC103; this fragment contains a 541 nucleotide region of soybean plastidic phosphoglucomutase, a 19 nucleotide artificial sequence at the 5' end and a 14 nucleotide artificial sequence at the 3' end.

SEQ ID NO:15 corresponds to the 541 nucleotide region of soybean plastidic phosphoglucomutase contained in SEQ ID NO:14.

SEQ ID NO:16 corresponds to the full-insert sequence (FIS) of corn clone p0075.cslaf22rb.

SEQ ID NO:17 corresponds to the nucleotide sequence of plasmid pKS133.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1, 3, 5, 7 and 9, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 contiguous nucleotides, preferably at least 40 contiguous nucleotides, most preferably at least 60 contiguous nucleotides derived from a nucleotide sequence selected from the group consisting of SEQ ID NOs:1, 3, 5, 7, and 9, and the complement of such nucleotide sequences may be used in methods of selecting an isolated polynucleotide that affects the expression of a plastidic phosphoglucomutase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403-410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15: 1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refer to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 560 amino acids having at least 95% identity based on the Clustal method of alignment when compared to a polypeptide selected from the group consisting of SEQ ID NOs:2, 4, 8, and 10 or (b) a second nucleotide sequence comprising the complement of the first nucleotide sequence.

Preferably, the nucleotide sequence comprises a nucleic acid sequence selected from the group consisting of SEQ ID NOs:1, 3, 7, and 9, that codes for the polypeptide selected from the group consisting of SEQ ID NOs:2, 4, 8, and 10.

Nucleic acid fragments encoding at least a substantial portion of several plastidic phosphoglucomutase proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other plastidic phosphoglucomutases, either as cDNAs or genomic DNAs, could be isolated directly by using all or a substantial portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 contiguous nucleotides, preferably at least 40 contiguous nucleotides, most preferably at least 60 contiguous nucleotides derived from a nucleotide sequence selected from the group consisting of SEQ ID NOs: 1, 3, 5, 7, and 9, and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a plastidic phosphoglucomutase polypeptide, preferably a substantial portion of a plant plastidic phosphoglucomutase polypeptide, comprising the steps of: synthesizing an oligonucleotide primer comprising a nucleotide sequence of at least 30 contiguous nucleotides, preferably at least 40 contiguous nucleotides, most preferably at least 60 contiguous nucleotides derived from a nucleotide sequence selected from the group consisting of SEQ ID NOs: 1, 3, 5, 7, and 9, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a plastidic phosphoglucomutase polypeptide.

Availability of the instant nucleotide and deduced amino acid sequences facilitates immunological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of starch and soluble carbohydrate biosynthesis in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 560 amino acids that has at least 95% identity based on the Clustal method of alignment when compared to a polypeptide selected from the group consisting of SEQ ID NOs:2, 4, 8 and 10.

The instant polypeptides (or substantial portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded plastidic phosphoglucomutase protein. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1: 174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various cattail, corn, rice and soybean tissues were prepared. The characteristics of the libraries are described below.

TABLE 2 cDNA Libraries from Cattail, Corn, Rice and Soybean

| Library | Tissue | Clone |
|---|---|---|
| etr1c | Cattail (*Typha latifolia*) root | etr1c.pk005.f8 |
| p0075 | Corn, root/leaf material from dark-grown 7 day old Seedlings | p0075.cslaf22f |
| | | p0075.cslaf22rb |
| p0128 | Corn, pooled primary and secondary immature ear | p0128.cpicz81r |
| rdi1c | Rice (*Oryza sativa*, Nipponbare) developing inflorescence at mitotic stage | rdi1c.pk001.a22 |
| rth1c | Rice leaf inoculated with *Magnaporta grisea* | rth1c.pk009.k14f |
| sdp3c | Soybean developing pods 8-9 mm | sdp3c.pk003.e22 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding plastidic phosphoglucomutase proteins were identified by conducting BLAST (Basic Local Alignment Search Tool; Altschul et al. (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Plastidic Phosphoglucomutase Proteins

The BLASTX search using the EST sequences from clones listed in Table 3 revealed similarity of the polypeptides encoded by the cDNAs to plastidic phosphoglucomutase from *Brassica napus* (NCBI Identifier No. gi 6272125) and *Pisum sativum* (NCBI Identifier No. gi 6272283 and NCBI Identifier No. gi 10190529). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, an EST and PCR, or an FIS and PCR ("CGS"):

TABLE 3

BLAST Results for Sequences Encoding Polypeptides Homologous to *Brassica napus* and *Pisum sativum* Plastidic Phosphoglucomutase

| Clone | Status | BLAST pLog Score |
|---|---|---|
| etr1c.pk005.f8 (FIS) | CGS | >254.00 (gi 6272125; *B. napus*) |
| Contig Composed of: | CGS | >254.00 (gi 6272283; *P. sativum*) |
| p0075.cslaf22f (EST) | | |
| p0075.cslaf22rb (EST) | | |
| p0128.cpicz81r (EST) | | |
| rth1c.pk009.k14f (EST) | EST | 58.00 (gi 6272283; *P. sativum*) |
| sdp3c.pk003.e22 (EST and PCR Fragments) | CGS | >254.00 (gi 6272283; *P. sativum*) |
| rdi1c.pk001.a22 (FIS) | CGS | 180.00 (gi 10190529; *P. sativum*) |

The data in Table 4 represents a calculation of the percent identity of the amino acid sequences set forth in SEQ ID NOs:2, 4, 6, 8, and 10, and the *Brassica napus* and *Pisum sativum* sequences.

TABLE 4

Percent Identity of Amino Acid Sequences Deduced From the Nucleotide Sequences of cDNA Clones Encoding Polypeptides Homologous to *Brassica napus* and *Pisum sativum* Plastidic Phosphoglucomutase

| SEQ ID NO. | Percent Identity to |
|---|---|
| 2 | 79% (gi 6272125; *B. napus*) |
| 4 | 77% (gi 6272283; *P. sativum*) |
| 6 | 80% (gi 6272283; *P. sativum*) |
| 8 | 90% (gi 6272283; *P. sativum*) |
| 10 | 76% (gi 10190529; *P. sativum*) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode a substantial portion of a plastidic phosphoglucomutase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue☐; Stratagene). Bacterial transformants can be screened by restriction enzyme digestion of plasmid DNA and limited nucleotide sequence analysis using the dideoxy chain termination method (Sequenase☐ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35 S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 □m in diameter) are coated with DNA using the following technique. Ten □g of plasmid DNAs are added to 50 □L of a suspension of gold particles (60 mg per mL). Calcium chloride (50 □L of a 2.5 M solution) and spermidine free base (20 □L of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 □L of absolute ethanol, centrifuged again and the supernatant removed. The ethanol rinse is performed again and the particles resuspended in a final volume of 30 □L of ethanol. An aliquot (5 □L) of the DNA-coated gold particles can be placed in the center of a Kapton□ flying disc (Bio-Rad Labs). The particles are then accelerated into the corn tissue with a Biolistic□ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Genes in Dicot Cells

A seed-specific construct composed of the promoter and transcription terminator from the gene encoding the □ subunit of the seed storage protein phaseolin from the bean *Phaseolus vulgaris* (Doyle et al. (1986) *J. Biol. Chem.* 261: 9228-9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL of liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic□ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 □L of a 60 mg/mL 1 □m gold particle suspension is added (in order): 5 □L DNA (1 □g/□L), 20 □L spermidine (0.1 M), and 50 □L CaCl$_2$ (2.5 M). The particle preparation is then agitated for three minutes, spun in a microfuge for 10 seconds and the supernatant removed. The DNA-coated particles are then washed once in 400 □L 70% ethanol and resuspended in 40 □L of anhydrous ethanol. The DNA/particle suspension can be sonicated three times for one second each. Five □L of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches of mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG□ low melting agarose gel (FMC). Buffer and agarose contain 10 □g/mL ethidium bromide for visualization of the DNA fragment. The fragment can then be purified from the agarose gel by digestion with GELase□ (Epicentre Technologies) according to the manufacturer's instructions, ethanol precipitated, dried and resuspended in 20 □L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 □g/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113-130). Cultures are grown in LB medium containing ampicillin (100 mg/L) at 25° C. At an optical density at 600 nm of approximately 1, IPTG (isopropylthio-□-galactoside, the inducer) can be added to a final concentration of 0.4 mM and incubation can be continued for 3 h at 25° C. Cells are then harvested by centrifugation and re-suspended in 50 □L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One □g of protein from the soluble fraction of the culture can be separated by SDS-polyacrylamide gel electrophoresis. Gels can be observed for protein bands migrating at the expected molecular weight.

Example 7

Transformation of Somatic Soybean Embryo Cultures

Generic Stable Soybean Transformation Protocol:

Soybean embryogenic suspension cultures are maintained in 35 ml liquid media (SB55 or SBP6) on a rotary shaker, 150 rpm, at 28° C. with mixed fluorescent and incandescent lights on a 16:8 h day/night schedule. Cultures are subcultured every four weeks by inoculating approximately 35 mg of tissue into 35 ml of liquid medium.

TABLE 1

| Stock Solutions (g/L): MS Sulfate 100X Stock | |
|---|---|
| $MgSO_4 \, 7H_2O$ | 37.0 |
| $MnSO_4 \, H_2O$ | 1.69 |
| $ZnSO_4 \, 7H_2O$ | 0.86 |
| $CuSO_4 \, 5H_2O$ | 0.0025 |
| MS Halides 100X Stock | |
| $CaCl_2 \, 2H_2O$ | 44.0 |
| KI | 0.083 |
| $CoCl_2 \, 6H_2O$ | 0.00125 |
| $KH_2PO_4$ | 17.0 |
| $H_3BO_3$ | 0.62 |
| $Na_2MoO_4 \, 2H_2O$ | 0.025 |
| MS FeEDTA 100X Stock | |
| $Na_2EDTA$ | 3.724 |
| $FeSO_4 \, 7H_2O$ | 2.784 |
| B5 Vitamin Stock | |
| 10 g m-inositol | |
| 100 mg nicotinic acid | |
| 100 mg pyridoxine HCl | |
| 1 g thiamine | |
| SB55 (per Liter, pH 5.7) | |
| 10 ml each MS stocks | |
| 1 ml B5 Vitamin stock | |
| 0.8 g $NH_4NO_3$ | |
| 3.033 g $KNO_3$ | |
| 1 ml 2,4-D (10 mg/mL stock) | |
| 60 g sucrose | |
| 0.667 g asparagine | |
| SBP6 | |
| same as SB55 except 0.5 ml 2,4-D | |
| SB103 (per Liter, pH 5.7) | |
| 1X MS Salts | |
| 6% maltose | |
| 750 mg $MgCl_2$ | |
| 0.2% Gelrite | |

Soybean embryogenic suspension cultures are transformed with plasmid DNA by the method of particle gun bombardment (Klein et al (1987) Nature 327:70). A DuPont Biolistic PDS1000/HE instrument (helium retrofit) is used for these transformations.

To 50 ml of a 60 mg/ml 1 □m gold particle suspension is added (in order); 5 □l DNA(1 □g/□l), 20 □l spermidine (0.1 M), and 50 □l CaCl$_2$ (2.5 M). The particle preparation is agitated for 3 min, spun in a microfuge for 10 sec and the supernatant removed. The DNA-coated particles are then washed once in 400 □l 70% ethanol and resuspended in 40 □l of anhydrous ethanol. The DNA/particle suspension is sonicated three times for 1 sec each. Five □l of the DNA-coated gold particles are then loaded on each macro carrier disk. For selection, a plasmid conferring resistance to hygromycin phosphotransferase (HPT) may be co-bombarded with the silencing construct of interest.

Approximately 300-400 mg of a four week old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1000 psi and the chamber is evacuated to a vacuum of 28 inches of mercury. The tissue is placed approximately 3.5 inches away from the retaining screen and bombarded three times. Following bombardment, the tissue is placed back into liquid and cultured as described above.

Eleven days post bombardment, the liquid media is exchanged with fresh SB55 containing 50 mg/ml hygromycin. The selective media is refreshed weekly. Seven weeks post bombardment, green, transformed tissue is observed growing from untransformed, necrotic embryogenic clusters. Isolated green tissue is removed and inoculated into individual flasks to generate new, clonally propagated, transformed embryogenic suspension cultures. Thus each new line is treated as an independent transformation event. These suspensions can then be maintained as suspensions of embryos maintained in an immature developmental stage or regenerated into whole plants by maturation and germination of individual somatic embryos.

Independent lines of transformed embryogenic clusters are removed from liquid culture and placed on a solid agar media (SB103) containing no hormones or antibiotics. Embryos are cultured for four weeks at 26° C. with mixed fluorescent and incandescent lights on a 16:8 h day/night schedule. During this period, individual embryos are removed from the clusters and screened for alterations in gene expression.

It should be noted that any detectable phenotype, resulting from the co-suppression of a target gene, can be screened at this stage. This would include, but not be limited to, alterations in protein content, carbohydrate content, growth rate, viability, or the ability to develop normally into a soybean plant.

Example 8

Plasmid DNAs for "Complementary Region" Co-Suppression

The plasmids used in these experiments were made using standard cloning methods well known to those skilled in the art (Sambrook et al (1989) Molecular Cloning, CSHL Press, New York). A starting plasmid pKS18HH (U.S. Pat. No. 5,846,784 the contents of which are hereby incorporated by reference) contains a hygromycin B phosphotransferase (HPT) obtained from E. coli strain W677 under the control of a T7 promoter and the 35S cauliflower mosaic virus promoter. Plasmid pKS18HH thus contains the T7 promoter/HPT/T7 terminator cassette for expression of the HPT enzyme in certain strains of E. coli, such as NovaBlue(DE3) [from Novagen], that are lysogenic for lambda DE3 (which carries the T7 RNA Polymerase gene under lacV5 control). Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pKS18HH also contains three unique restiction endonuclease sites suitable for the cloning other chimeric genes into this vector. Plasmid ZBL100(PCT Application No. WO 00/11176 published on Mar. 2, 2000) is a derivative of pKS18HH with a reduced NOS 3' terminator. Plasmid pKS67 is a ZBL100 derivative with the insertion of a beta-conglycinin promoter, in front of a NotI cloning site, followed by a phaseolin 3' terminator (described in PCT Application No. WO 94/11516, published on May 26, 1994).

The 2.5 kb plasmid pKS17 contains pSP72 (obtained from Promega Biosystems) and the T7 promoter/HPT/T7 3' terminator region, and is the original vector into which the 3.2 kb BamHI-SalI fragment containing the 35S/HPT/NOS cassette was cloned to form pKS18HH. The plasmid pKS102 is a pKS17 derivative that is digested with XhoI and SalI, treated with mung-bean nuclease to generate blunt ends, and ligated to insert the following linker:

```
GGCGCGCCAAGCTTGGATCCGTCGACGGCGCGCC
Artificial DNA No. 1
```

The plasmid pKS83 has the 2.3 kb BamHI fragment of ML70 containing the Kti3 promoter/NotI/Kti3 3' terminator region (described in PCT Application No. WO 94/11516, published on May 26, 1994) ligated into the BamHI site of pKS17.

Example 9

Suppression by ELVISLIVES Complementary Region

Constructs have now been made which have "synthetic complementary regions" (SCR). In this example the target sequence is placed between complementary sequences that are not known to be part of any biologically derived gene or genome (i.e. sequences that are "synthetic" or conjured up from the mind of the inventor). The target DNA would therefore be in the sense or antisense orientation and the complementary RNA would be unrelated to any known nucleic acid sequence. It is possible to design a standard "suppression vector" into which pieces of any target gene for suppression could be dropped. The plasmids pKS106, pKS124, and pKS133 (SEQ ID NO:17) exemplify this. One skilled in the art will appreciate that all of the plasmid vectors contain antibiotic selection genes such as, but not limited to, hygromycin phosphotransferase with promoters such as the T7 inducible promoter.

pKS106 uses the beta-conglycinin promoter while the pKS124 and pKS133 plasmids use the Kti promoter, both of these promoters exhibit strong tissue specific expression in the seeds of soybean. pKS106 uses a 3' termination region from the phaseolin gene, and pKS124 and pKS133 use a Kti 3' termination region. pKS106 and pKS124 have single copies of the 36 nucleotide EagI-ELVISLIVES sequence surrounding a NotI site (the amino acids given in parentheses are back-translated from the complementary strand): SEQ ID NO:19

```
EagI E L V I S L I V E S NotI
CGGCCG GAG CTG GTC ATC TCG CTC ATC GTC GAG TCG
GCGGCCGC (S) (E) (V) (I) (L) (S) (I) (V) (L) (E) EagI
CGA CTC GAC GAT GAG CGA GAT GAC CAG CTC CGGCCG
``` pKS133 has 2X copies of ELVISLIVES surrounding the NotI site: Artificial DNA No. 3

```
EagI E L V I S L I V E S EagI E L V I S
cggccggagctggtcatctcgctcatcgtcgagtcg gcggccg gagctggtcatctcg L I V E S NotI (S)(E)(V)(I)(L)(S)(I)(V)(L)(E) EagI
ctcatcgtcgagtcg gcggccgc cgactcgacgatgagcgagatgacc agctc cggccgc (S)(E)(V)(I)(L)(S)(I)(V)(L)(E) EagI
cgactcgacgatgagcgagatgaccagctc cggccg
```

The idea is that the single EL linker (SCR) can be duplicated to increase stem lengths in increments of approximately 40 nucleotides. A series of vectors will cover the SCR lengths between 40 bp and the 300 bp. Various target gene lengths are also under evaluation. It is believed that certain combinations of target lengths and complementary region lengths will give optimum suppression of the target, although preliminary results would indicate that the suppression phenomenon works well over a wide range of sizes and sequences. It is also believed that the lengths and ratios providing optimum suppression may vary somewhat given different target sequences and/or complementary regions.

The plasmid pKS106 is made by putting the EagI fragment of ELVISLIVES (SEQ ID NO:19) into the NotI site of pKS67. The ELVISLIVES fragment is made by PCR using two primers and no other DNA:

```
Artificial DNA No. 4
5'-GAATTCCGGCCGGAGCTGGTCATCTCGCTCATCGTCGAGTCGGCGGC

CGCCGACTCGACGATGAGCGAGATGACCAGCTCCGGCCGGAATTC-3'

Artificial DNA No. 5
5'-GAATTCCGGCCGGAG-3'
```

The product of the PCR reaction is digested with EagI (5'-CGGCCG-3') and then ligated into NotI digested pKS67. The term "ELVISLIVES" and "EL" are used interchangeably herein.

Additional plasmids can be used to test this example. For example, pKS121 contains the Kti3 promoter/NotI/Kti3 3' terminator fragment analogous to pKS83 inserted into the BamHI-SalI digested pKS102. The EagI digested ELVISLIVES cloning site made from SEQ ID NOs:14 and 15 is inserted into the NotI site of pKS121 to form pKS124. The EagI digested EL PCR product can be ligated into NotI digested pKS124 to form the 2XEL plasmid, pKS133 (SEQ ID NO:17), containing two copies of ELVISLIVES. An additional 2XEL vector, pKS151, is similar to pKS133 except for the addition of a second hygromycin phosphotransferase gene with a 35S-CaMV promoter. Any synthetic sequence, or naturally occurring sequence, can be used in an analogous manner. The addition of a 574 base pair NotI fragment (SEQ ID NO:14) into a NotI-digested pKS133 produces pTC103. The 574 base pair Not I fragment (SEQ ID NO:14) contains a 541 base pair region (SEQ ID NO:15) of the soybean plastid phosphoglucomutase coding region (SEQ ID NO:8).

Example 10

Down Regulation of Plastidic Phosphoglucomutase in Soybean

Soybean was transformed with the plasmid DNA, pTC103, and transgenic lines were selected. Transgenic lines were screened for down regulation of plastidic phosphoglucomutase in soybean. The screening assay involved iodine staining for the presence or absence of starch in immature seeds (mid-pod stage). The method involved harvesting half of the seed, and putting that seed on dry ice and storing at −80 C. The other half of the seed was placed in 100% ethanol overnight, and subsequently stained with water:lugol (4:1) solution for 10 to 30 minutes at room temperature. Lugol is an iodine/potassium iodide solution, commercially available from Sigma.

Four out of nineteen events showed a clear reduction in iodine staining indicating a reduction in starch content. This may reflect a 21% cosuppression success with the hairpin construct. Three additional events showed potential reduction in iodine staining, although the differences in staining were subtle. The segregation patterns of events 100-2-1 and 108-3-1 are consistent with a theoretical segregation of a dominant co-suppression (1:3).

TABLE 5

Summary of Iodine Screen

|  | sum |
|---|---|
| + Events | 4 |
| − Events | 12 |
| ? Events | 3 |
| Total Events Analyzed | 19 |
| Events with no plants/sterile/dwarf | 2 |
| Total Events | 27 |

TABLE 6

Seed segregation information of potential positive PGM events.

| Event | Plant | D:L seed ratio | Note |
|---|---|---|---|
| 100-2-1 | 1 | 1:5 | clear positive |
|  | 2 | 3:2 | clear positive |
|  | 3 | 1:5 | clear positive |
| 108-3-1 | 1 | 0:6 | clear positive |
|  | 2 | 2:4 | clear positive |
|  | 3 | 1:5 | clear positive |
| 105-2-3 | 1 | 4:0 | negative |
|  | 2 | 1:5 | clear positive |
| 105-1-6 | 1 | 4:0 | negative |
|  | 3 | 2:2 | clear positive |

TABLE 6-continued

Seed segregation information of potential positive PGM events.

| Event | Plant | D:L seed ratio | Note |
|---|---|---|---|
| 105-1-1 | 1 | 4:2 | D/L |
|  | 2 | 0:6 | D/L |
|  | 3 | 6:0 | D/L |
| 101-2-6 | 1 | 6:0 | D/L |
|  | 3 | 2:3 | D/L |
| 102-3-3 | 1 | 2:3 | D/L |
|  | 2 | 3:0 | D/L |

D = dark blue stain,
L = light blue of no stain,
D/L in between dark and light stain

What is claimed is:

1. An isolated polynucleotide comprising:
   (a) a nucleotide sequence encoding a polypeptide having phosphoglucomutase activity, wherein the amino acid sequence of the polypeptide and the amino acid sequence of SEQ ID NO:4 have at least 95% sequence identity based on the Clustal alignment method with pairwise alignment default parameters of KTUPLE=1, GAP PENALTY=3, WINDOW=5 and DIAGONALS SAVED=5, further wherein the amino acid sequence is 605 amino acids long; or
   (b) the full-length complement of the nucleotide sequence of (a).

2. The isolated polynucleotide of claim 1, wherein the polypeptide comprises the amino acid sequence of SEQ ID NO:4.

3. The isolated polynucleotide of claim 1, wherein the nucleotide sequence comprises the nucleotide sequence of SEQ ID NO:3.

4. A recombinant DNA construct comprising the polynucleotide of claim 1 operably linked to a regulatory sequence.

5. A vector comprising the polynucleotide of claim 1.

6. A method for transforming a cell comprising transforming a cell with the polynucleotide of claim 1.

7. A cell comprising the recombinant DNA construct of claim 4.

8. A method for producing a transgenic plant comprising transforming a plant cell with the recombinant DNA construct of claim 4 and regenerating a transgenic plant from the transformed plant cell.

9. A plant comprising the recombinant DNA construct of claim 4.

10. A seed comprising the recombinant DNA construct of claim 4.

11. A method for positive selection of a transformed cell comprising:
   (a) transforming a host cell with the recombinant DNA construct of claim 4; and
   (b) growing the transformed host cell under conditions which allow expression of a polynucleotide in an amount sufficient to complement a null mutant to provide a positive selection means.

12. The method of claim 11 wherein the host cell is a plant.

13. The method of claim 12 wherein the plant cell is a monocot.

14. The method of claim 12 wherein the plant cell is a dicot.

15. A method of altering the level of expression of a plastidic phosphoglucomutase protein in a host cell comprising:
   (a) transforming a host cell with the recombinant DNA construct of claim 4; and
   (b) growing the transformed host cell produced in step (a) under conditions that are suitable for expression of the recombinant DNA construct wherein expression of the recombinant DNA construct results in production of altered levels of a plastidic phosphoglucomutase polypeptide in the transformed host cell.

* * * * *

SEQUENCE LISTING

<160> NUMBER OF SEQ ID NOS: 22

<210> SEQ ID NO 1
<211> LENGTH: 2112
<212> TYPE: DNA
<213> ORGANISM: Typha latifolia

<400> SEQUENCE: 1

```
gcaccagctc gttatcgcca cttatcgctc tctcaatctc tctctccata cttgcaagaa      60
atggcaatgt cggtgcctac tatgaggttg catcccctcg tcccctcttc gaagcttctc     120
tctccctcct cttcgtcgcc ggcggtgctg gtctcttccc ggattcctct cctctctctt     180
aggaggccaa acctgaggtt ctccgtcaag gctaccgctt cttccactcc gtccacggcc     240
gaaagcataa agatcaagtc gatacccacc aagccagtag aagggcagaa gactgggact     300
agcggattaa ggaagaaggt taaggttttc cagcaggaga attacttggc aaactggatt     360
caggcactgt ttaattcctt gccgctggag gattacaaga atggattgct ggttttggga     420
ggtgatgggc ggtactttaa ccgagaggct gcacagataa tcatcaagat tgctgctgga     480
aatggtgttg gaaaaattct tgttggcagg gatggtatca tgtcaactcc tgctgtatct     540
gcagtaatac gtaaacagaa ggcaaatggt ggttttatca tgagtgcaag ccataatcct     600
ggtggtccgg actatgattg gggcattaag tttaattaca gcagtggaca acctgcacct     660
gaatcaatta ctgacaaaat ctacggtaac actctttcga tttctgaaat aaaaatatca     720
gatatacctg atattgatct atccagtcta ggtgttacca attatggcaa cttttctgtg     780
gaggtggtag accctgtttc agattacttg gagttaatgg agaatgtgtt tgattttcag     840
ctcatcaaag gtcttctttc tcgatctgat ttcaggttta catttgatgc gatgcatgca     900
gtaacaggtg catatgcaaa acctatcttt gtggaacggc ttcgagctag cccggattgt     960
gttttaaatg gagtgcctct tgaagatttt ggccatggtc acccagaccc caatctgacg    1020
tatgctaagg agcttgttga tgtaatgtat accacagatg cacctgatct aggagcagca    1080
agtgatggtg atggtgatcg aaacatgatt cttggaagac gtttctttgt tacaccatca    1140
gattctgttg caatgattgc cgctaatgca caggcggcta ttccttattt ccaagctggt    1200
cccaaaggac ttgctaggtc tatgccaaca agcggtgctc ttgatcgtgt agccgaaaaa    1260
ttgaaccttc cattctttga ggttccaact ggttggaagt tttttggaaa tctgatggat    1320
gctgggaagt tgtccatctg tggggaggaa agttttggca caggttctga tcacatccgg    1380
gagaaggatg gcatctgggc tgttttggct tggcttttcca taattgcgta cagaaacaag    1440
```

-continued

```
gacaaaaaga ttggagagaa attagtctct gttgaagata ttgctaagga gcactgggca    1500
aaatatggca ggaacttctt ttctcgatat gattacgaag aatgcgaatc ggaaggagca    1560
aataaaatga tgcagcacct tagggacttt atctcgacaa gcaagcctgg agaacaatat    1620
ggaaattata ctcttcaatt ttcagatgac ttttcctaca ctgaccctgt agacggcagt    1680
gtagcatcca agcaagggct acgatttgtt ttcacagatg gatcaagggt tatctatcgt    1740
ctctcgggta ctggatcggc cggtgcaact atacggatat atgttgaaca attcgagccc    1800
gatgtctcca agcatgatgt ggatgcacaa gcagcattaa agcctttgat agacctcgca    1860
ttgtcgatat caaagctgaa ggaatttacc ggcagggaga agcctacagt cattacatga    1920
gctgcatgga tggctaggta gcacgtatat tctttattt tatgtgatgg cacgtccatt     1980
ttgctaataa agtaataatg taaagaagtc attacgcaga gtactagtct tttattatgc    2040
gatgcaacaa tcactcagtt ttgctattaa aaatgggact cacttctttc ccagaaaaaa    2100
aaaaaaaaaa aa                                                         2112
```

<210> SEQ ID NO 2
<211> LENGTH: 639
<212> TYPE: PRT
<213> ORGANISM: Typha latifolia

<400> SEQUENCE: 2

```
Ala Pro Ala Arg Tyr Arg His Leu Ser Leu Ser Gln Ser Leu Ser Pro
  1               5                  10                  15

Tyr Leu Gln Glu Met Ala Met Ser Val Pro Thr Met Arg Leu His Pro
             20                  25                  30

Leu Val Pro Ser Ser Lys Leu Leu Ser Pro Ser Ser Ser Pro Ala
         35                  40                  45

Val Leu Val Ser Ser Arg Ile Pro Leu Leu Ser Leu Arg Arg Pro Asn
     50                  55                  60

Leu Arg Phe Ser Val Lys Ala Thr Ala Ser Ser Thr Pro Ser Thr Ala
 65                  70                  75                  80

Glu Ser Ile Lys Ile Lys Ser Ile Pro Thr Lys Pro Val Glu Gly Gln
                 85                  90                  95

Lys Thr Gly Thr Ser Gly Leu Arg Lys Lys Val Lys Val Phe Gln Gln
            100                 105                 110

Glu Asn Tyr Leu Ala Asn Trp Ile Gln Ala Leu Phe Asn Ser Leu Pro
        115                 120                 125

Leu Glu Asp Tyr Lys Asn Gly Leu Leu Val Leu Gly Gly Asp Gly Arg
    130                 135                 140

Tyr Phe Asn Arg Glu Ala Ala Gln Ile Ile Ile Lys Ile Ala Ala Gly
145                 150                 155                 160

Asn Gly Val Gly Lys Ile Leu Val Gly Arg Asp Gly Ile Met Ser Thr
                165                 170                 175

Pro Ala Val Ser Ala Val Ile Arg Lys Gln Lys Ala Asn Gly Gly Phe
            180                 185                 190

Ile Met Ser Ala Ser His Asn Pro Gly Gly Pro Asp Tyr Asp Trp Gly
        195                 200                 205

Ile Lys Phe Asn Tyr Ser Ser Gly Gln Pro Ala Pro Glu Ser Ile Thr
    210                 215                 220

Asp Lys Ile Tyr Gly Asn Thr Leu Ser Ile Ser Glu Ile Lys Ile Ser
225                 230                 235                 240

Asp Ile Pro Asp Ile Asp Leu Ser Ser Leu Gly Val Thr Asn Tyr Gly
                245                 250                 255
```

Asn Phe Ser Val Glu Val Asp Pro Val Ser Asp Tyr Leu Glu Leu
            260                 265                 270

Met Glu Asn Val Phe Asp Phe Gln Leu Ile Lys Gly Leu Leu Ser Arg
        275                 280                 285

Ser Asp Phe Arg Phe Thr Phe Asp Ala Met His Ala Val Thr Gly Ala
290                 295                 300

Tyr Ala Lys Pro Ile Phe Val Glu Arg Leu Arg Ala Ser Pro Asp Cys
305                 310                 315                 320

Val Leu Asn Gly Val Pro Leu Glu Asp Phe Gly His Gly His Pro Asp
                325                 330                 335

Pro Asn Leu Thr Tyr Ala Lys Glu Leu Val Asp Val Met Tyr Thr Thr
            340                 345                 350

Asp Ala Pro Asp Leu Gly Ala Ala Ser Asp Gly Asp Gly Asp Arg Asn
        355                 360                 365

Met Ile Leu Gly Arg Arg Phe Phe Val Thr Pro Ser Asp Ser Val Ala
370                 375                 380

Met Ile Ala Ala Asn Ala Gln Ala Ala Ile Pro Tyr Phe Gln Ala Gly
385                 390                 395                 400

Pro Lys Gly Leu Ala Arg Ser Met Pro Thr Ser Gly Ala Leu Asp Arg
                405                 410                 415

Val Ala Glu Lys Leu Asn Leu Pro Phe Phe Glu Val Pro Thr Gly Trp
            420                 425                 430

Lys Phe Phe Gly Asn Leu Met Asp Ala Gly Lys Leu Ser Ile Cys Gly
        435                 440                 445

Glu Glu Ser Phe Gly Thr Gly Ser Asp His Ile Arg Glu Lys Asp Gly
450                 455                 460

Ile Trp Ala Val Leu Ala Trp Leu Ser Ile Ala Tyr Arg Asn Lys
465                 470                 475                 480

Asp Lys Lys Ile Gly Glu Lys Leu Val Ser Val Glu Asp Ile Ala Lys
                485                 490                 495

Glu His Trp Ala Lys Tyr Gly Arg Asn Phe Phe Ser Arg Tyr Asp Tyr
            500                 505                 510

Glu Glu Cys Glu Ser Glu Gly Ala Asn Lys Met Met Gln His Leu Arg
        515                 520                 525

Asp Phe Ile Ser Thr Ser Lys Pro Gly Glu Gln Tyr Gly Asn Tyr Thr
530                 535                 540

Leu Gln Phe Ser Asp Asp Phe Ser Tyr Thr Asp Pro Val Asp Gly Ser
545                 550                 555                 560

Val Ala Ser Lys Gln Gly Leu Arg Phe Val Phe Thr Asp Gly Ser Arg
                565                 570                 575

Val Ile Tyr Arg Leu Ser Gly Thr Gly Ser Ala Gly Ala Thr Ile Arg
            580                 585                 590

Ile Tyr Val Glu Gln Phe Glu Pro Asp Val Ser Lys His Asp Val Asp
        595                 600                 605

Ala Gln Ala Ala Leu Lys Pro Leu Ile Asp Leu Ala Leu Ser Ile Ser
610                 615                 620

Lys Leu Lys Glu Phe Thr Gly Arg Glu Lys Pro Thr Val Ile Thr
625                 630                 635

<210> SEQ ID NO 3
<211> LENGTH: 1951
<212> TYPE: DNA
<213> ORGANISM: Zea mays

<400> SEQUENCE: 3

```
ccacgcgtcc gcacaaactg ccctcgcggc ctcgcccgtc gccctctcg atcacttctc      60
tcccgacact ctctcactcc cgtgtcgtgt ctagcgccga cggcgttgct accggagccg     120
gccagcggcc acgatgccta caatgcacgc gcttcgccta tgcccgctgc tctccaccat    180
ccgatccaca ccaccgcggg ccactgccgc agcccgccag ggcgcgctct cgtcgcccg     240
ctgctcctcc gccgggacgc cgtcagccgc ccaggcgctc aagatcagtt caatcccgac    300
caagccagtt gagggcaga agactgggac tagtggcctg aggaaaaagg tgaaagtatt    360
ccagcaggag aactaccttg ctaattggat tcaggctcta ttcaattcct gccccctga    420
agattatgtg ggtgcaaccc ttgtacttgg gggtgatggc cggtactta caaggaggc    480
tgctcagatc atcattaaga ttgcagctgg aaatggagtt cagaagatca tagttggcag    540
gaatggtcta ctgtcaacac ctgctgtatc tgctgtaatt cgtaaaagaa aagccaatgg    600
cggctttatc atgagtgcaa gccataatcc aggtggacca gacaatgact ggggtattaa    660
gtttaactac agcagtggac agccagcacc ggagacgatt actgatcaaa tttatggaaa    720
cacactatca atttctgaaa taaaaacagc agacattcct gatactgatt tgtcctctgt    780
tggagttgta agctatggtg atttcgccat agaagtgata gatcctgttt cagattacct    840
tgaactaatg gagaatgtgt ttgacttcca acttatcaag gatttgcttt ctcggcctga    900
tttcaggttc atatttgatg caatgcatgc aattactggt gcgtatgccg gacccatttt    960
tgttgagaaa cttggagctg atccggactg catattaaat ggggtgcctc ttgaagattt   1020
tggaaatggc catccagatc caaatctaac ttacgctaag gagcttgttt ttactatgtt   1080
tggaacccat gcacctgact ttggtgcagc aagtgatggt gatggtgatc ggaacatgat   1140
tcttgggaaa aggttcttta ttaccccatc agactctgtt gcaataattg cagccaatgc   1200
acagacagca attccttatt ccagttttgg tacaaaagga ctcgcgagat caatgccaac   1260
cagtggtgct cttgatcgtg ttgccgagaa attgaatgtt ccattctttg aggttccaac   1320
aggctggaaa tttttttggca acctaatgga tgcaggaaaa ttgtctattt gtggagagga   1380
aagttttggg actggatctg atcacatcag agagaaggat ggcatctggg ctgttctggc   1440
ttggctttcc atacttgcac accggaacaa ggataagaag gtcggagaga gattagtgtc   1500
agttgaagat attgctatgg agcactggaa aacctatgga aggaatttct tttctagata   1560
cgattatgag gcgtgtgaat cacacagtgc aaaccagatg atggatcacc ttagagatgt   1620
tatggcaaat agcaagcctg agagaaata cggaaattac accctccaat ttgctgatga   1680
tttcagctat actgatcctg tagacggtag tacggtatca aaacaaggac ttcgatttgt   1740
tttcactgat ggatctagga ttatcttccg gctttcggga accggatctg ctggagctac   1800
tatccgcctc tacatagaac aatttgaatc tgatatctcg aagcatagtc tcgatgctca   1860
aacagctttg aagcctttaa tagacctggc tttgtctgtt tcgaagctca aggacttcac   1920
aggaagagag aaacctactg tcataacata g                                  1951
```

<210> SEQ ID NO 4
<211> LENGTH: 605
<212> TYPE: PRT
<213> ORGANISM: Zea mays

<400> SEQUENCE: 4

```
Met Pro Thr Met His Ala Leu Arg Leu Cys Pro Leu Leu Ser Thr Ile
 1               5                  10                  15

Arg Ser Thr Pro Pro Arg Ala Thr Ala Ala Ala Arg Gln Gly Ala Leu
             20                  25                  30
```

```
Phe Val Ala Arg Cys Ser Ser Ala Gly Thr Pro Ser Ala Ala Gln Ala
             35                  40                  45

Leu Lys Ile Ser Ser Ile Pro Thr Lys Pro Val Glu Gly Gln Lys Thr
     50                  55                  60

Gly Thr Ser Gly Leu Arg Lys Lys Val Lys Val Phe Gln Gln Glu Asn
 65                  70                  75                  80

Tyr Leu Ala Asn Trp Ile Gln Ala Leu Phe Asn Ser Leu Pro Pro Glu
                 85                  90                  95

Asp Tyr Val Gly Ala Thr Leu Val Leu Gly Asp Gly Arg Tyr Phe
                100                 105                 110

Asn Lys Glu Ala Ala Gln Ile Ile Lys Ile Ala Ala Gly Asn Gly
             115                 120                 125

Val Gln Lys Ile Ile Val Gly Arg Asn Gly Leu Leu Ser Thr Pro Ala
     130                 135                 140

Val Ser Ala Val Ile Arg Lys Arg Lys Ala Asn Gly Gly Phe Ile Met
145                 150                 155                 160

Ser Ala Ser His Asn Pro Gly Gly Pro Asp Asn Asp Trp Gly Ile Lys
                165                 170                 175

Phe Asn Tyr Ser Ser Gly Gln Pro Ala Pro Glu Thr Ile Thr Asp Gln
                180                 185                 190

Ile Tyr Gly Asn Thr Leu Ser Ile Ser Glu Ile Lys Thr Ala Asp Ile
         195                 200                 205

Pro Asp Thr Asp Leu Ser Ser Val Gly Val Val Ser Tyr Gly Asp Phe
     210                 215                 220

Ala Ile Glu Val Ile Asp Pro Val Ser Asp Tyr Leu Glu Leu Met Glu
225                 230                 235                 240

Asn Val Phe Asp Phe Gln Leu Ile Lys Asp Leu Leu Ser Arg Pro Asp
                245                 250                 255

Phe Arg Phe Ile Phe Asp Ala Met His Ala Ile Thr Gly Ala Tyr Ala
                260                 265                 270

Gly Pro Ile Phe Val Glu Lys Leu Gly Ala Asp Pro Asp Cys Ile Leu
            275                 280                 285

Asn Gly Val Pro Leu Glu Asp Phe Gly Asn Gly His Pro Asp Pro Asn
    290                 295                 300

Leu Thr Tyr Ala Lys Glu Leu Val Phe Thr Met Phe Gly Thr His Ala
305                 310                 315                 320

Pro Asp Phe Gly Ala Ala Ser Asp Gly Asp Gly Asp Arg Asn Met Ile
                325                 330                 335

Leu Gly Lys Arg Phe Phe Ile Thr Pro Ser Asp Ser Val Ala Ile Ile
            340                 345                 350

Ala Ala Asn Ala Gln Thr Ala Ile Pro Tyr Phe Gln Phe Gly Thr Lys
        355                 360                 365

Gly Leu Ala Arg Ser Met Pro Thr Ser Gly Ala Leu Asp Arg Val Ala
    370                 375                 380

Glu Lys Leu Asn Val Pro Phe Phe Glu Val Pro Thr Gly Trp Lys Phe
385                 390                 395                 400

Phe Gly Asn Leu Met Asp Ala Gly Lys Leu Ser Ile Cys Gly Glu Glu
                405                 410                 415

Ser Phe Gly Thr Gly Ser Asp His Ile Arg Glu Lys Asp Gly Ile Trp
            420                 425                 430

Ala Val Leu Ala Trp Leu Ser Ile Leu Ala His Arg Asn Lys Asp Lys
        435                 440                 445

Lys Val Gly Glu Arg Leu Val Ser Val Glu Asp Ile Ala Met Glu His
```

```
                450             455             460
Trp Lys Thr Tyr Gly Arg Asn Phe Phe Ser Arg Tyr Asp Tyr Glu Ala
465                 470                 475                 480

Cys Glu Ser His Ser Ala Asn Gln Met Met Asp His Leu Arg Asp Val
                485                 490                 495

Met Ala Asn Ser Lys Pro Gly Glu Lys Tyr Gly Asn Tyr Thr Leu Gln
            500                 505                 510

Phe Ala Asp Asp Phe Ser Tyr Thr Asp Pro Val Asp Gly Ser Thr Val
        515                 520                 525

Ser Lys Gln Gly Leu Arg Phe Val Phe Thr Asp Gly Ser Arg Ile Ile
    530                 535                 540

Phe Arg Leu Ser Gly Thr Gly Ser Ala Gly Ala Thr Ile Arg Leu Tyr
545                 550                 555                 560

Ile Glu Gln Phe Glu Ser Asp Ile Ser Lys His Ser Leu Asp Ala Gln
                565                 570                 575

Thr Ala Leu Lys Pro Leu Ile Asp Leu Ala Leu Ser Val Ser Lys Leu
            580                 585                 590

Lys Asp Phe Thr Gly Arg Glu Lys Pro Thr Val Ile Thr
        595                 600                 605

<210> SEQ ID NO 5
<211> LENGTH: 573
<212> TYPE: DNA
<213> ORGANISM: Oryza sativa

<400> SEQUENCE: 5
tgatggagca tcttagagat gtgatcgcaa aaagcaagcc tggagagaaa tatggaaact      60 ataccettca gtttgccgat gatttcagtt acactgatcc ggtggatggt agcactgtat     120
ctaaacaagg gcttcgattt gtattcaccg atggatctag gattatcttc cgcctttcgg     180
gaaccggatc tgctggagca acaatccgta tatacattga gcaattcgag tctgatgcct     240
caaagcatga tctggatgca caaatagctt tgaagccttt aatagaccta gctctatctg     300
tttcaaagtt gaaggacttc actgggaaga gataagccta ctgtcataac ataaacatac     360
cggtgacatt agcaatgtta ccacctgggt attctttat tccttgttt ttaaaagccc       420 cttccaaccg atgaaccaat aatgttatcc taagccaagt tttgtactga gttgatggca     480
aactgtatcc tgggggtac tttcaattga acataagtat gcaaggaatg aataaagctt      540
ttaaaagcaa aaaaaaaaa aaaaaaaaaa aaa                                   573

<210> SEQ ID NO 6
<211> LENGTH: 117
<212> TYPE: PRT
<213> ORGANISM: Oryza sativa
<220> FEATURE:
<221> NAME/KEY: UNSURE
<222> LOCATION: (108)
<223> OTHER INFORMATION: Xaa can be any naturally occurring amino acid

<400> SEQUENCE: 6

Met Glu His Leu Arg Asp Val Ile Ala Lys Ser Lys Pro Gly Glu Lys
1               5                   10                  15

Tyr Gly Asn Tyr Thr Leu Gln Phe Ala Asp Asp Phe Ser Tyr Thr Asp
            20                  25                  30

Pro Val Asp Gly Ser Thr Val Ser Lys Gln Gly Leu Arg Phe Val Phe
        35                  40                  45

Thr Asp Gly Ser Arg Ile Ile Phe Arg Leu Ser Gly Thr Gly Ser Ala
    50                  55                  60
```

```
Gly Ala Thr Ile Arg Ile Tyr Ile Glu Gln Phe Glu Ser Asp Ala Ser
 65                  70                  75                  80

Lys His Asp Leu Asp Ala Gln Ile Ala Leu Lys Pro Leu Ile Asp Leu
             85                  90                  95

Ala Leu Ser Val Ser Lys Leu Lys Asp Phe Thr Xaa Gly Arg Asp Lys
        100                 105                 110

Pro Thr Val Ile Thr
        115

<210> SEQ ID NO 7
<211> LENGTH: 2204
<212> TYPE: DNA
<213> ORGANISM: Glycine max
<220> FEATURE:
<221> NAME/KEY: unsure
<222> LOCATION: (7)
<223> OTHER INFORMATION: n = A, C, G, or T
<220> FEATURE:
<221> NAME/KEY: unsure
<222> LOCATION: (1332)
<223> OTHER INFORMATION: n = A, C, G, or T

<400> SEQUENCE: 7
aaaactnttt ggaaccctcc agcatttcat ttctcatcat caatggcttt ctcttgtaaa      60
cttgacagct tcattctctc tgcctataaa ccccaaaact ccattctccc actttcaatc     120
caaccttcct ccttccttcc atctccttct tctttgaagc ctcagaagct tcccttcaga     180
attcgctatg gttctaccat cagagccacg tcatcatcct caaccccttc cgcaaccatt     240
gccgaacctg aaggcattaa gattaaatcg attccaacca agcccattga tggacaaaag     300
actggaacca gtgggcttcg aaagaaggtg aaagtgttta gcaagacaa ttaccttgca     360
aattggatcc aggctctgtt taattcattg ccaccggagg actacaagaa tggtttgttg     420
gtgttgggag tgatggtcg atactttaat caggaagctg cacagataat aatcaaaatt     480
gctgctggaa atggtgttgg aaaaattctg gttggaaagg aaggtatttt gtcaacacca     540
gccgttctg ctgttataag aaagagaaag gcaaatggtg gatttattat gagtgcaagc     600
cataatcctg gcggacctga atatgattgg ggtattaagt ttaattacag cagtggacaa     660
cctgcaccag aatccatcac tgacaagatt tatggaaata ccctgtcgat ctctgagata     720
aagatagctg acattcctga tgttgattta tcaaaagttg gggttacaaa ttttggaagc     780
ttcagtgtgg aagtaataga cccagtttct gactatctgg agctattgga gacagtattt     840
gattttcagc taatcagagg tcttctttca cgtccagatt ttaggtttat atttgatgcc     900
atgcatgcag ttactggtgc ttatgctaaa cccatcttcg ttgataaact cggtgctagt     960
ctggattcaa tttcaaatgg aatcccttg gaagattttg acatggcca tcctgatcct    1020
aatctaacat atgcgaagga tcttgtcgac attctgtatg ctgaaaatgg acctgatttt    1080
ggagctgcca gtgatgggga tggtgataga aatatgattt taggaagaag tttctttgta    1140
actccttcag actctgtagc agttattgca gccaatgcaa gagaagcgat tccatacttc    1200
aagaacggtg ttaagggtct tgctcgatca atgccaccaa gcggtgctct ggaccgtgtt    1260
gctaaaaaat tgaacctccc tttctttgag gtccccactg gttggaaatt ttttgggaat    1320
cttatggatg cnggaaattt gtccgtttgc ggggaagaga ttttggaac aggttctgat    1380
cacattcgtg agaaagatgg catctgggct gtcttagctt ggctttctat tattgcacat    1440
cgcaacaaag acaagaatcc cggggagaaa ttgatctccg tatctgacgt tgtgatggag    1500
cactgggcaa cttatggaag gaatttcttc tctagatatg actacgagga atgtgaatct    1560
```

```
gaaggtgcca ataagatgat agaatacccta cgagatattt tgtctaagag caagcctggt    1620
gatcagtatg gaagttatgt tctccagttt gcagatgatt ttacatacac cgatcctgta    1680
gatggaagtg tggtatcaaa acaaggtgtt cggtttgttt ttacagacgg ttcaaggatt    1740
atatatcgtt tatcaggaac tggttctgca ggggctacgg ttagagtgta cattgaacag    1800
tttgaaccag atgtctctaa acatgatgtt gatgctcaaa ttgccttaaa accattaata    1860
gatttggcaa tatccgtgtc aaagctcaaa gacttcacag ggagggagaa gcctacagtc    1920
atcacataat ggacaattcc acaaccactt gatcaagttg ttatatgttc caaggtgtgc    1980
tctaagttga gtgcatacgc aggttgttta ttgcatgcct atccatatct gagctcgctc    2040
gagttcggtc acttttggtt gttcaagaat tttggagcga taggtcccct gtaaaatatg    2100
ctacttatat atttatgtgc aaagtatgaa gcaccgacgt gcaacaaaat aataataaaa    2160
aagaatagtt tgctgctcta aggagctagg cctttcaaaa aaaa                     2204
```

<210> SEQ ID NO 8
<211> LENGTH: 628
<212> TYPE: PRT
<213> ORGANISM: Glycine max

<400> SEQUENCE: 8

```
Met Ala Phe Ser Cys Lys Leu Asp Ser Phe Ile Leu Ser Ala Tyr Lys
  1               5                  10                  15

Pro Gln Asn Ser Ile Leu Pro Leu Ser Ile Gln Pro Ser Ser Phe Leu
             20                  25                  30

Pro Ser Pro Ser Ser Leu Lys Pro Gln Lys Leu Pro Phe Arg Ile Arg
         35                  40                  45

Tyr Gly Ser Thr Ile Arg Ala Thr Ser Ser Ser Thr Pro Ser Ala
     50                  55                  60

Thr Ile Ala Glu Pro Glu Gly Ile Lys Ile Lys Ser Ile Pro Thr Lys
 65                  70                  75                  80

Pro Ile Asp Gly Gln Lys Thr Gly Thr Ser Gly Leu Arg Lys Lys Val
                 85                  90                  95

Lys Val Phe Met Gln Asp Asn Tyr Leu Ala Asn Trp Ile Gln Ala Leu
            100                 105                 110

Phe Asn Ser Leu Pro Pro Glu Asp Tyr Lys Asn Gly Leu Leu Val Leu
        115                 120                 125

Gly Gly Asp Gly Arg Tyr Phe Asn Gln Glu Ala Ala Gln Ile Ile Ile
    130                 135                 140

Lys Ile Ala Ala Gly Asn Gly Val Gly Lys Ile Leu Val Gly Lys Glu
145                 150                 155                 160

Gly Ile Leu Ser Thr Pro Ala Val Ser Ala Val Ile Arg Lys Arg Lys
                165                 170                 175

Ala Asn Gly Gly Phe Ile Met Ser Ala Ser His Asn Pro Gly Gly Pro
            180                 185                 190

Glu Tyr Asp Trp Gly Ile Lys Phe Asn Tyr Ser Ser Gly Gln Pro Ala
        195                 200                 205

Pro Glu Ser Ile Thr Asp Lys Ile Tyr Gly Asn Thr Leu Ser Ile Ser
    210                 215                 220

Glu Ile Lys Ile Ala Asp Ile Pro Asp Val Asp Leu Ser Lys Val Gly
225                 230                 235                 240

Val Thr Asn Phe Gly Ser Phe Ser Val Glu Val Ile Asp Pro Val Ser
                245                 250                 255

Asp Tyr Leu Glu Leu Leu Glu Thr Val Phe Asp Phe Gln Leu Ile Arg
```

```
                260                 265                 270
Gly Leu Leu Ser Arg Pro Asp Phe Arg Phe Ile Phe Asp Ala Met His
                275                 280                 285
Ala Val Thr Gly Ala Tyr Ala Lys Pro Ile Phe Val Asp Lys Leu Gly
                290                 295                 300
Ala Ser Leu Asp Ser Ile Ser Asn Gly Ile Pro Leu Glu Asp Phe Gly
305                 310                 315                 320
His Gly His Pro Asp Pro Asn Leu Thr Tyr Ala Lys Asp Leu Val Asp
                325                 330                 335
Ile Leu Tyr Ala Glu Asn Gly Pro Asp Phe Gly Ala Ala Ser Asp Gly
                340                 345                 350
Asp Gly Asp Arg Asn Met Ile Leu Gly Arg Ser Phe Phe Val Thr Pro
                355                 360                 365
Ser Asp Ser Val Ala Val Ile Ala Ala Asn Ala Arg Glu Ala Ile Pro
                370                 375                 380
Tyr Phe Lys Asn Gly Val Lys Gly Leu Ala Arg Ser Met Pro Pro Ser
385                 390                 395                 400
Gly Ala Leu Asp Arg Val Ala Lys Lys Leu Asn Leu Pro Phe Phe Glu
                405                 410                 415
Val Pro Thr Gly Trp Lys Phe Phe Gly Asn Leu Met Asp Ala Gly Asn
                420                 425                 430
Leu Ser Val Cys Gly Glu Glu Ser Phe Gly Thr Gly Ser Asp His Ile
                435                 440                 445
Arg Glu Lys Asp Gly Ile Trp Ala Val Leu Ala Trp Leu Ser Ile Ile
                450                 455                 460
Ala His Arg Asn Lys Asp Lys Asn Pro Gly Glu Lys Leu Ile Ser Val
465                 470                 475                 480
Ser Asp Val Val Met Glu His Trp Ala Thr Tyr Gly Arg Asn Phe Phe
                485                 490                 495
Ser Arg Tyr Asp Tyr Glu Glu Cys Glu Ser Gly Ala Asn Lys Met
                500                 505                 510
Ile Glu Tyr Leu Arg Asp Ile Leu Ser Lys Ser Lys Pro Gly Asp Gln
                515                 520                 525
Tyr Gly Ser Tyr Val Leu Gln Phe Ala Asp Asp Phe Thr Tyr Thr Asp
                530                 535                 540
Pro Val Asp Gly Ser Val Ser Lys Gln Gly Val Arg Phe Val Phe
545                 550                 555                 560
Thr Asp Gly Ser Arg Ile Ile Tyr Arg Leu Ser Gly Thr Gly Ser Ala
                565                 570                 575
Gly Ala Thr Val Arg Val Tyr Ile Glu Gln Phe Glu Pro Asp Val Ser
                580                 585                 590
Lys His Asp Val Asp Ala Gln Ile Ala Leu Lys Pro Leu Ile Asp Leu
                595                 600                 605
Ala Ile Ser Val Ser Lys Leu Lys Asp Phe Thr Gly Arg Glu Lys Pro
                610                 615                 620
Thr Val Ile Thr
625

<210> SEQ ID NO 9
<211> LENGTH: 2197
<212> TYPE: DNA
<213> ORGANISM: Oryza sativa

<400> SEQUENCE: 9
gcacgaggct tgcccgcttc cttccgcggt gcaagcgcaa caccacctca cctcactccc        60
```

```
cttctcgcct cttctcccct tctccacctc ctcttctctc cgcgtggcgg tggcattgcc    120
ggccgccgca tcgtctcggg atggcctcgc acgcgctccg cctccacccg ctgctcttct    180
ccgccgccgc cgcgcgcccg gctccgctcg cggcgcggcc cggtggtggt gcccgccggg    240
tccaccgccg ccactctctc gccgtcgtcc ggtgctcctc ctccgccgcc caggcgctca    300
agatcaagtc gattccgacc aagcccgttg aggggcagaa gacccgggacc agtgggttga   360
ggaagaaggt gaaagtgttc cagcaggaga attacctcgc taattggatt caggctctgt    420
tcaattcatt gccccgggag gattatgttg gtgaaccct tgtgcttggt ggtgatggcc     480
gatactttaa caaggatgct gctcagatta tcactaaaat gcagctggg aatggtgttg     540
ggaagatcct agttggcagg aacggtctgc tgtcaacgcc tgctgtatct gcagtaattc    600
gtaaaagaca agccaatggt ggcttcatca tgagtgcaag ccataatcca ggtgggccag    660
ataatgattg gggtatcaag ttcaactata gcagtgggca gccagcacca gagacaatta    720
ccgaccaaat atatggaaac acactttcga tttctgaaat aaaaacggca gatattcctg    780
atgttgattt gtcctctcta ggagttgtaa gctatggtga tttcaccgtt gaagtgatag    840
accctgtctt ggactacctt gagctaatgg agaatgtgtt tgacttccaa cttatcaagg    900
gcttgttgtc tcggccagat ttcaggtttg tatttgatgc catgcatgct gtgactggtg    960
catatgcgga tcctattttt gttgagaaac ttggagctga tccggactat atattaaatg   1020
gtgttccact tgaagatttt ggcaatggtc accctgatcc taatttaact tatgccaaag   1080
agcttgtgtt taccatgttt ggaagcggag cacctgactt tggtgcagca agtgatggtg   1140
atggtgatcg aaacatgatt cttggaagaa ggttctttgt tacaccatca gactctgttg   1200
caataattgc agcgaatgca caggcagcaa ttccttattt ccaatctggt ccaaaaggtc   1260
ttgctagatc aatgccaacg agtggtgctc ttgatcgtgt agctgataaa ttgaatgttc   1320
cgttctttga ggtaccaaca ggatggaaat tttttggaaa cctaatggat gcaggtaaat   1380
tgtctatatg tggagaggaa agttttggga caggatctga tcacatcagg gagaaggatg   1440
gcatatgggc tgttctagct tggctgtcca tacttgcaca ccggaacaag gataagaagg   1500
ccggggagag attagtgtca gtggaagatg tagctaggga acactgggca acctatggaa   1560
ggaatttctt ctccagatat gattatgagg agtgtgaatc tgagagtgca aataagatga   1620
tggagcatct tagagatgtg atcgcaaaaa gcaagcctgg agagaaatat ggaaactata   1680
cccttcagtt tgccgatgat ttcagttaca ctgatccggt ggatggtagc actgtatcta   1740
aacaagggct tcgatttgta ttcaccgatg atctaggat tatcttccgc ctttcgggaa    1800
ccggatctgc tggagcaaca atccgtatat acattgagca attcgagtct gatgcctcaa   1860
agcatgatct ggatgcacaa atagctttga agcctttaat agacctagct ctatctgttt   1920
caaagttgaa ggacttcact ggaagagata agcctactgt cataacataa acataccggt   1980
gacattagca atgttaccac ctgtgtattc ttttattct ttgtttttat agccccttcc    2040
aaccgatgaa ccaataatgt aatcttaggc caagttttgt actgagttga tggcaaactg   2100
tatcttggag gtacctttca ttgaacatag tatgcaggaa tgaataagct tttagagcaa   2160
tggtacatat ttcagaacaa aaaaaaaaa aaaaaaa                             2197
```

<210> SEQ ID NO 10
<211> LENGTH: 655
<212> TYPE: PRT
<213> ORGANISM: Oryza sativa

<400> SEQUENCE: 10

-continued

```
Thr Arg Leu Ala Arg Phe Leu Pro Arg Cys Lys Arg Asn Thr Thr Ser
 1               5                  10                  15
Pro His Ser Pro Ser Arg Leu Phe Ser Pro Ser Pro Pro Leu Leu
                20                  25                  30
Ser Ala Trp Arg Trp His Cys Arg Pro Pro His Arg Leu Gly Met Ala
                35                  40                  45
Ser His Ala Leu Arg Leu His Pro Leu Leu Phe Ser Ala Ala Ala Ala
         50                  55                  60
Arg Pro Ala Pro Leu Ala Ala Arg Pro Gly Gly Ala Arg Arg Val
 65                  70                  75                  80
His Arg Arg His Ser Leu Ala Val Val Arg Cys Ser Ser Ala Ala
                85                  90                  95
Gln Ala Leu Lys Ile Lys Ser Ile Pro Thr Lys Pro Val Glu Gly Gln
                100                 105                 110
Lys Thr Gly Thr Ser Gly Leu Arg Lys Lys Val Lys Val Phe Gln Gln
                115                 120                 125
Glu Asn Tyr Leu Ala Asn Trp Ile Gln Ala Leu Phe Asn Ser Leu Pro
         130                 135                 140
Pro Glu Asp Tyr Val Gly Gly Thr Leu Val Leu Gly Gly Asp Gly Arg
145                 150                 155                 160
Tyr Phe Asn Lys Asp Ala Ala Gln Ile Ile Thr Lys Ile Ala Ala Gly
                165                 170                 175
Asn Gly Val Gly Lys Ile Leu Val Gly Arg Asn Gly Leu Leu Ser Thr
                180                 185                 190
Pro Ala Val Ser Ala Val Ile Arg Lys Arg Gln Ala Asn Gly Gly Phe
         195                 200                 205
Ile Met Ser Ala Ser His Asn Pro Gly Gly Pro Asp Asn Asp Trp Gly
         210                 215                 220
Ile Lys Phe Asn Tyr Ser Ser Gly Gln Pro Ala Pro Glu Thr Ile Thr
225                 230                 235                 240
Asp Gln Ile Tyr Gly Asn Thr Leu Ser Ile Ser Glu Ile Lys Thr Ala
                245                 250                 255
Asp Ile Pro Asp Val Asp Leu Ser Ser Leu Gly Val Val Ser Tyr Gly
                260                 265                 270
Asp Phe Thr Val Glu Val Ile Asp Pro Val Leu Asp Tyr Leu Glu Leu
                275                 280                 285
Met Glu Asn Val Phe Asp Phe Gln Leu Ile Lys Gly Leu Leu Ser Arg
         290                 295                 300
Pro Asp Phe Arg Phe Val Phe Asp Ala Met His Ala Val Thr Gly Ala
305                 310                 315                 320
Tyr Ala Asp Pro Ile Phe Val Glu Lys Leu Gly Ala Asp Pro Asp Tyr
                325                 330                 335
Ile Leu Asn Gly Val Pro Leu Glu Asp Phe Gly Asn His Pro Asp
                340                 345                 350
Pro Asn Leu Thr Tyr Ala Lys Glu Leu Val Phe Thr Met Phe Gly Ser
         355                 360                 365
Gly Ala Pro Asp Phe Gly Ala Ala Ser Asp Gly Asp Gly Asp Arg Asn
         370                 375                 380
Met Ile Leu Gly Arg Arg Phe Phe Val Thr Pro Ser Asp Ser Val Ala
385                 390                 395                 400
Ile Ile Ala Ala Asn Ala Gln Ala Ala Ile Pro Tyr Phe Gln Ser Gly
                405                 410                 415
Pro Lys Gly Leu Ala Arg Ser Met Pro Thr Ser Gly Ala Leu Asp Arg
```

```
                420             425             430
Val Ala Asp Lys Leu Asn Val Pro Phe Phe Glu Val Pro Thr Gly Trp
            435                 440                 445
Lys Phe Phe Gly Asn Leu Met Asp Ala Gly Lys Leu Ser Ile Cys Gly
        450                 455                 460
Glu Glu Ser Phe Gly Thr Gly Ser Asp His Ile Arg Glu Lys Asp Gly
465                 470                 475                 480
Ile Trp Ala Val Leu Ala Trp Leu Ser Ile Leu Ala His Arg Asn Lys
                485                 490                 495
Asp Lys Lys Ala Gly Glu Arg Leu Val Ser Val Glu Asp Val Ala Arg
            500                 505                 510
Glu His Trp Ala Thr Tyr Gly Arg Asn Phe Phe Ser Arg Tyr Asp Tyr
        515                 520                 525
Glu Glu Cys Glu Ser Glu Ser Ala Asn Lys Met Met Glu His Leu Arg
530                 535                 540
Asp Val Ile Ala Lys Ser Lys Pro Gly Glu Lys Tyr Gly Asn Tyr Thr
545                 550                 555                 560
Leu Gln Phe Ala Asp Asp Phe Ser Tyr Thr Asp Pro Val Asp Gly Ser
                565                 570                 575
Thr Val Ser Lys Gln Gly Leu Arg Phe Val Phe Thr Asp Gly Ser Arg
            580                 585                 590
Ile Ile Phe Arg Leu Ser Gly Thr Gly Ser Ala Gly Ala Thr Ile Arg
        595                 600                 605
Ile Tyr Ile Glu Gln Phe Glu Ser Asp Ala Ser Lys His Asp Leu Asp
        610                 615                 620
Ala Gln Ile Ala Leu Lys Pro Leu Ile Asp Leu Ala Leu Ser Val Ser
625                 630                 635                 640
Lys Leu Lys Asp Phe Thr Gly Arg Asp Lys Pro Thr Val Ile Thr
                645                 650                 655

<210> SEQ ID NO 11
<211> LENGTH: 629
<212> TYPE: PRT
<213> ORGANISM: Brassica napus

<400> SEQUENCE: 11

Met Ser Ser Thr Tyr Ala Arg Phe Asp Thr Val Phe Leu Leu Ser Arg
1               5                   10                  15
Phe Ala Gly Ala Lys Tyr Ser Pro Leu Trp Pro Ser Ser Ser Ser Ser
            20                  25                  30
Ser His Ser Ser Leu Leu Ser Gly Ile His Leu Arg Ala Lys Pro
        35                  40                  45
Asn Ser Arg Leu Arg Ser Val Thr Gly Ala Ser Ser Ser Ser Ser Gly
    50                  55                  60
Pro Ile Ile Ala Gly Ser Glu Ser Ile Glu Ile Lys Ser Leu Pro Thr
65                  70                  75                  80
Lys Pro Ile Glu Gly Gln Lys Thr Gly Thr Ser Gly Leu Arg Lys Lys
                85                  90                  95
Val Lys Val Phe Met Gln Asp Asn Tyr Leu Ala Asn Trp Ile Gln Ala
            100                 105                 110
Leu Phe Asn Ser Leu Pro Leu Glu Asp Tyr Lys Asp Ala Thr Leu Val
        115                 120                 125
Leu Gly Gly Asp Gly Arg Tyr Phe Asn Lys Glu Ala Ser Gln Ile Ile
    130                 135                 140
Ile Lys Ile Ala Ala Gly Asn Gly Val Gly Lys Ile Leu Val Gly Gln
```

-continued

```
            145                 150                 155                 160
        Glu Gly Ile Leu Ser Thr Pro Ala Val Ser Ala Val Ile Arg Lys Arg
                            165                 170                 175
        Lys Ala Asn Gly Gly Phe Ile Met Ser Ala Ser His Asn Pro Gly Gly
                            180                 185                 190
        Pro Glu Tyr Asp Trp Gly Ile Lys Phe Asn Tyr Ser Ser Gly Gln Pro
                            195                 200                 205
        Ala Pro Glu Ser Ile Thr Asp Lys Ile Tyr Gly Asn Thr Leu Ser Ile
                            210                 215                 220
        Ser Glu Ile Lys Val Ala Glu Ile Pro Asp Ile Asp Leu Ser His Val
        225                 230                 235                 240
        Gly Val Thr Lys Tyr Gly Asn Phe Ser Val Glu Val Ile Asp Pro Ile
                            245                 250                 255
        Ser Asp Tyr Leu Glu Leu Met Glu Asp Val Phe Asp Phe Asp Leu Ile
                            260                 265                 270
        Arg Gly Leu Leu Ser Arg Ser Asp Phe Gly Phe Met Phe Asp Ala Met
                            275                 280                 285
        His Ala Val Thr Gly Ala Tyr Ala Lys Pro Ile Phe Val Asp Asn Leu
                            290                 295                 300
        Glu Ala Lys Pro Asp Ser Ile Ser Asn Gly Val Pro Leu Glu Asp Phe
        305                 310                 315                 320
        Gly His Gly His Pro Asp Pro Asn Leu Thr Tyr Ala Lys Asp Leu Val
                            325                 330                 335
        Asp Val Met Tyr Arg Asp Asp Gly Pro Asp Phe Gly Ala Ala Ser Asp
                            340                 345                 350
        Gly Asp Gly Asp Arg Asn Met Val Leu Gly Asn Lys Phe Phe Val Thr
                            355                 360                 365
        Pro Ser Asp Ser Val Ala Ile Ile Ala Ala Asn Ala Gln Glu Ala Ile
                            370                 375                 380
        Pro Tyr Phe Arg Ala Gly Pro Lys Gly Leu Ala Arg Ser Met Pro Thr
        385                 390                 395                 400
        Ser Gly Ala Leu Asp Arg Val Ala Glu Lys Leu Lys Leu Pro Phe Phe
                            405                 410                 415
        Glu Val Pro Thr Gly Trp Lys Phe Phe Gly Asn Leu Met Asp Ala Gly
                            420                 425                 430
        Lys Leu Ser Ile Cys Gly Glu Glu Ser Phe Gly Thr Gly Ser Asp His
                            435                 440                 445
        Ile Arg Glu Lys Asp Gly Ile Trp Ala Val Leu Ala Trp Leu Ser Ile
                            450                 455                 460
        Leu Ala His Arg Ile Lys Asp Lys Lys Pro Gly Glu Lys Leu Val Ser
        465                 470                 475                 480
        Val Ala Asp Val Val Asn Glu Tyr Trp Ala Thr Tyr Gly Arg Asn Phe
                            485                 490                 495
        Phe Ser Arg Tyr Asp Tyr Glu Glu Cys Glu Ser Glu Gly Ala Asn Lys
                            500                 505                 510
        Met Ile Glu Tyr Leu Arg Asp Ile Val Ala Lys Ser Lys Ala Gly Glu
                            515                 520                 525
        Asn Tyr Gly Asn Tyr Val Leu Gln Phe Ala Asp Phe Ser Tyr Lys
                            530                 535                 540
        Asp Pro Val Asp Gly Ser Val Ala Ser Lys Gln Gly Val Arg Phe Val
        545                 550                 555                 560
        Phe Thr Asp Gly Ser Arg Ile Ile Tyr Arg Leu Ser Gly Asn Gly Ser
                            565                 570                 575
```

```
Ala Gly Ala Thr Val Arg Ile Tyr Ile Glu Gln Phe Glu Pro Asp Val
            580                 585                 590

Ser Lys His Asp Val Asp Ala Gln Ile Ala Ile Lys Pro Leu Ile Asp
        595                 600                 605

Leu Ala Leu Ser Val Ser Lys Leu Lys Glu Phe Thr Gly Arg Glu Lys
610                 615                 620

Pro Thr Val Ile Thr
625

<210> SEQ ID NO 12
<211> LENGTH: 626
<212> TYPE: PRT
<213> ORGANISM: Pisum sativum

<400> SEQUENCE: 12

Met Ala Phe Cys Tyr Arg Leu Asp Asn Phe Ile Ile Ser Ala Phe Lys
  1               5                  10                  15

Pro Lys His Ser Asn Val Pro Leu Ser Ile His His Ser Ser Ser Asn
             20                  25                  30

Phe Pro Ser Phe Lys Val Gln Asn Phe Pro Phe Arg Val Arg Tyr Asn
         35                  40                  45

Ser Ala Ile Arg Ala Thr Ser Ser Ser Ser Thr Pro Thr Thr Ile
     50                  55                  60

Ala Glu Pro Asn Asp Ile Lys Ile Asn Ser Ile Pro Thr Lys Pro Ile
 65                  70                  75                  80

Glu Gly Gln Lys Thr Gly Thr Ser Gly Leu Arg Lys Lys Val Lys Val
                 85                  90                  95

Phe Lys Gln Glu Asn Tyr Leu Ala Asn Trp Ile Gln Ala Leu Phe Asn
            100                 105                 110

Ser Leu Pro Pro Glu Asp Tyr Lys Asn Gly Leu Leu Val Leu Gly Gly
        115                 120                 125

Asp Gly Arg Tyr Phe Asn Lys Glu Ala Ala Gln Ile Ile Ile Lys Ile
    130                 135                 140

Ala Ala Gly Asn Gly Val Gly Lys Ile Leu Val Gly Lys Glu Gly Ile
145                 150                 155                 160

Leu Ser Thr Pro Ala Val Ser Ala Val Ile Arg Lys Arg Glu Ala Asn
                165                 170                 175

Gly Gly Phe Ile Met Ser Ala Ser His Asn Pro Gly Gly Pro Glu Tyr
            180                 185                 190

Asp Trp Gly Ile Lys Phe Asn Tyr Ser Ser Gly Gln Pro Ala Pro Glu
        195                 200                 205

Ser Ile Thr Asp Lys Ile Tyr Gly Asn Thr Leu Ser Ile Ser Glu Ile
    210                 215                 220

Lys Ile Ala Asp Ile Pro Asp Val Asp Leu Ser Asn Val Gly Val Thr
225                 230                 235                 240

Lys Phe Gly Ser Phe Ser Val Glu Val Ile Asp Pro Val Ser Asp Tyr
                245                 250                 255

Leu Glu Leu Leu Glu Thr Val Phe Asp Phe Gln Leu Ile Lys Ser Leu
            260                 265                 270

Ile Ser Arg Pro Asp Phe Arg Phe Thr Phe Asp Ala Met His Ala Val
        275                 280                 285

Ala Gly Ala Tyr Ala Thr Pro Ile Phe Val Asp Lys Leu Ser Ala Ser
    290                 295                 300

Leu Asp Ser Ile Ser Asn Gly Ile Pro Leu Glu Asp Phe Gly His Gly
305                 310                 315                 320
```

```
His Pro Asp Pro Asn Leu Thr Tyr Ala Lys Asp Leu Val Lys Ile Met
            325                 330                 335

Tyr Ala Glu Asn Gly Pro Asp Phe Gly Ala Ala Ser Asp Gly Asp Gly
        340                 345                 350

Asp Arg Asn Met Ile Leu Gly Thr Ser Phe Phe Val Thr Pro Ser Asp
    355                 360                 365

Ser Val Ala Val Ile Ala Ala Asn Ala Lys Glu Ala Ile Pro Tyr Phe
370                 375                 380

Lys Asp Ser Ile Lys Gly Leu Ala Arg Ser Met Pro Thr Ser Gly Ala
385                 390                 395                 400

Leu Asp Arg Val Ala Glu Lys Leu Asn Leu Pro Phe Phe Glu Val Pro
                405                 410                 415

Thr Gly Trp Lys Phe Phe Gly Asn Leu Met Asp Ala Gly Asn Leu Ser
            420                 425                 430

Ile Cys Gly Glu Glu Ser Phe Gly Thr Gly Ser Asp His Ile Arg Glu
        435                 440                 445

Lys Asp Gly Ile Trp Ala Val Leu Ala Trp Leu Ser Ile Ile Ala His
    450                 455                 460

Arg Asn Lys Asp Thr Lys Pro Gly Glu Lys Leu Val Ser Val Ser Asp
465                 470                 475                 480

Val Val Lys Glu His Trp Ala Thr Tyr Gly Arg Asn Phe Phe Ser Arg
                485                 490                 495

Tyr Asp Tyr Glu Glu Cys Glu Ser Glu Gly Ala Asn Lys Met Ile Glu
            500                 505                 510

Tyr Leu Arg Glu Leu Leu Ser Lys Ser Lys Pro Gly Asp Lys Tyr Gly
        515                 520                 525

Ser Tyr Val Leu Gln Phe Ala Asp Asp Phe Thr Tyr Thr Asp Pro Val
    530                 535                 540

Asp Gly Ser Val Val Ser Lys Gln Gly Val Arg Phe Val Phe Thr Asp
545                 550                 555                 560

Gly Ser Arg Ile Ile Tyr Arg Leu Ser Gly Thr Gly Ser Ala Gly Ala
                565                 570                 575

Thr Val Arg Val Tyr Ile Glu Gln Phe Glu Pro Asp Val Ser Lys His
            580                 585                 590

Asp Val Asp Ala Gln Ile Ala Leu Lys Pro Leu Ile Asp Leu Ala Leu
        595                 600                 605

Ser Val Ser Lys Leu Lys Asp Phe Thr Gly Arg Glu Lys Pro Thr Val
    610                 615                 620

Ile Thr
625

<210> SEQ ID NO 13
<211> LENGTH: 626
<212> TYPE: PRT
<213> ORGANISM: Pisum sativum

<400> SEQUENCE: 13

Met Ala Phe Cys Tyr Arg Leu Asp Asn Phe Ile Ile Ser Ala Phe Lys
1               5                   10                  15

Pro Lys His Ser Asn Val Pro Leu Ser Ile His His Ser Ser Ser Asn
            20                  25                  30

Phe Pro Ser Phe Lys Val Gln Asn Phe Pro Phe Arg Val Arg Tyr Asn
        35                  40                  45

Ser Ala Ile Arg Ala Thr Ser Ser Ser Ser Thr Pro Thr Thr Ile
    50                  55                  60
```

```
Ala Glu Pro Asn Asp Ile Lys Ile Asn Ser Ile Pro Thr Lys Pro Ile
 65                  70                  75                  80

Glu Gly Gln Lys Thr Gly Thr Ser Gly Leu Arg Lys Lys Val Lys Val
                 85                  90                  95

Phe Lys Gln Glu Asn Tyr Leu Ala Asn Trp Ile Gln Ala Leu Phe Asn
            100                 105                 110

Ser Leu Pro Pro Glu Asp Tyr Lys Asn Gly Leu Leu Val Leu Gly Gly
        115                 120                 125

Asp Gly Arg Tyr Phe Asn Lys Glu Ala Ala Gln Ile Ile Ile Lys Ile
    130                 135                 140

Ala Ala Gly Asn Gly Val Gly Lys Ile Leu Val Gly Lys Glu Gly Ile
145                 150                 155                 160

Leu Ser Thr Pro Ala Val Ser Ala Val Ile Arg Lys Arg Glu Ala Asn
                165                 170                 175

Gly Gly Phe Ile Met Ser Ala Ser His Asn Pro Gly Gly Pro Glu Tyr
            180                 185                 190

Asp Trp Gly Ile Lys Phe Asn Tyr Ser Ser Gly Gln Pro Ala Pro Glu
        195                 200                 205

Ser Ile Thr Asp Lys Ile Tyr Gly Asn Thr Leu Ser Ile Ser Glu Ile
    210                 215                 220

Lys Ile Ala Asp Ile Pro Asp Val Asp Leu Ser Asn Val Gly Val Thr
225                 230                 235                 240

Lys Phe Gly Ser Phe Ser Val Glu Val Ile Asp Pro Val Ser Asp Tyr
                245                 250                 255

Leu Glu Leu Leu Glu Thr Val Phe Asp Phe Gln Leu Ile Lys Ser Leu
            260                 265                 270

Ile Ser Arg Pro Asp Phe Arg Phe Thr Phe Asp Ala Met His Ala Val
        275                 280                 285

Ala Gly Ala Tyr Ala Thr Pro Ile Phe Val Asp Lys Leu Gly Ala Ser
    290                 295                 300

Pro Asp Ser Ile Ser Asn Gly Ile Pro Leu Glu Asp Phe Gly His Gly
305                 310                 315                 320

His Pro Asp Pro Asn Leu Thr Tyr Ala Lys Asp Leu Val Asn Ile Met
                325                 330                 335

Tyr Ala Glu Asn Gly Pro Asp Phe Gly Ala Ala Ser Asp Gly Asp Gly
            340                 345                 350

Asp Arg Asn Met Ile Leu Gly Thr Ser Phe Phe Val Thr Pro Ser Asp
        355                 360                 365

Ser Val Ala Val Ile Ala Ala Asn Ala Lys Glu Ala Ile Pro Tyr Phe
    370                 375                 380

Lys Asp Ser Ile Lys Gly Leu Ala Arg Ser Met Pro Thr Ser Gly Ala
385                 390                 395                 400

Leu Asp Arg Val Ala Glu Lys Leu Asn Leu Pro Phe Phe Glu Val Pro
                405                 410                 415

Thr Gly Trp Lys Phe Phe Gly Asn Leu Met Asp Ala Gly Asn Leu Ser
            420                 425                 430

Ile Cys Gly Glu Glu Ser Phe Gly Thr Gly Ser Asp His Ile Arg Glu
        435                 440                 445

Lys Asp Gly Ile Trp Ala Val Leu Ala Trp Leu Ser Ile Ile Ala His
    450                 455                 460

Arg Asn Lys Asp Thr Lys Pro Gly Glu Lys Leu Val Ser Val Ser Asp
465                 470                 475                 480

Val Val Lys Glu His Trp Ala Thr Tyr Gly Arg Asn Phe Phe Ser Arg
                485                 490                 495
```

Tyr Asp Tyr Glu Glu Cys Glu Ser Glu Gly Ala Asn Lys Met Ile Glu
              500                 505                 510

Tyr Leu Arg Glu Leu Leu Ser Lys Ser Lys Pro Gly Asp Lys Tyr Gly
         515                 520                 525

Ser Tyr Val Leu Gln Phe Ala Asp Asp Tyr Thr Tyr Thr Asp Pro Val
         530                 535                 540

Asp Gly Ser Val Val Ser Lys Gln Gly Val Arg Phe Val Phe Thr Asp
545                 550                 555                 560

Gly Ser Arg Ile Ile Tyr Arg Leu Ser Gly Thr Gly Ser Ala Gly Ala
             565                 570                 575

Thr Val Arg Val Tyr Ile Glu Gln Phe Glu Pro Asp Val Ser Lys His
         580                 585                 590

Asp Val Asp Ala Gln Ile Ala Leu Lys Pro Leu Ile Asp Leu Ala Leu
         595                 600                 605

Ser Val Ser Lys Leu Lys Asp Phe Thr Gly Arg Glu Lys Pro Thr Val
         610                 615                 620

Ile Thr
625

<210> SEQ ID NO 14
<211> LENGTH: 574
<212> TYPE: DNA
<213> ORGANISM: synthetic construct

<400> SEQUENCE: 14
ggccgctgag ctgatttaag atttatcaaa agttggggtt acaaattttg gaagcttcag      60
tgtggaagta atagacccag tttctgacta tctggagcta ttggagacag tatttgattt     120
tcagctaatc agaggtcttc tttcacgtcc agattttagg tttatatttg atgccatgca     180
tgcagttact ggtgcttatg ctaaacccat cttcgttgat aaactcggtg ctagtctgga     240
ttcaatttca aatggaatcc cttttggaaga ttttggacat ggccatcctg atcctaatct     300
aacatatgcg aaggatcttg tcgacattct gtatgctgaa atggacctg attttggagc      360 tgccagtgat ggggatggtg atagaaatat gattttagga agaagtttct ttgtaactcc     420
ttcagactct gtagcagtta ttgcagccaa tgcaagagaa gcgattccat acttcaagaa     480
cggtgttaag ggtcttgctc gatcaatgcc aacaagcggt gctctggacc gtgctgctaa     540
aaaattgaac ctcccctttct gagctgattt aagc                                574

<210> SEQ ID NO 15
<211> LENGTH: 541
<212> TYPE: DNA
<213> ORGANISM: Glycine max

<400> SEQUENCE: 15
gatttatcaa aagttggggt tacaaatttt ggaagcttca gtgtggaagt aatagaccca      60
gtttctgact atctggagct attggagaca gtatttgatt tcagctaat cagaggtctt      120 ctttcacgtc cagattttag gtttatattt gatgccatgc atgcagttac tggtgcttat     180
gctaaaccca tcttcgttga taaactcggt gctagtctgg attcaattc aaatggaatc      240 cctttggaag attttggaca tggccatcct gatcctaatc taacatatgc gaaggatctt     300
gtcgacattc tgtatgctga aatggacct gattttggag ctgccagtga tggggatggt      360
gatagaaata tgattttagg aagaagtttc tttgtaactc cttcagactc tgtagcagtt     420
attgcagcca atgcaagaga agcgattcca tacttcaaga acggtgttaa gggtcttgct     480

| | |
|---|---|
| cgatcaatgc caacaagcgg tgctctggac cgtgctgcta aaaaattgaa cctcccttc | 540 |
| t | 541 |

<210> SEQ ID NO 16
<211> LENGTH: 2401
<212> TYPE: DNA
<213> ORGANISM: Zea mays

<400> SEQUENCE: 16

| | |
|---|---|
| ccacgcgtcc gcacaaactg ccctcgcggc ctcgcccgtc gcccctctcg atcacttctc | 60 |
| tcccgacact ctctcactcc cgtgtcgtgt ctagcgccga cggcgttgct accggagccg | 120 |
| gccagcggcc acgatgccta caatgcacgc gcttcgccta tgcccgctgc tctccaccat | 180 |
| ccgatccaca ccaccgcggg ccactgccgc agcccgccag ggcgcgctct tcgtcgcccg | 240 |
| ctgctcctcc gccgggacgc cgtcagccgc ccaggcgctc aagatcagtt caatcccgac | 300 |
| caagccagtt gaggggcaga agactgggac tagtggcctg aggaaaaagg tgaaagtatt | 360 |
| ccagcaggag aactaccttg ctaattggat tcaggctcta ttcaattcct tgcccctga | 420 |
| agattatgtg ggtgcaaccc ttgtacttgg gggtgatggc cggtacttta caaggaggc | 480 |
| tgctcagatc atcattaaga ttgcagctgg aaatggagtt cagaagatca tagttggcag | 540 |
| gaatggtcta ctgtcaacac ctgctgtatc tgctgtaatt cgtaaaagaa aagccaatgg | 600 |
| cggctttatc atgagtgcaa gccataatcc aggtggacca acaatgact ggggtattaa | 660 |
| gtttaactac agcagtggac agccagcacc ggagacgatt actgatcaaa tttatggaaa | 720 |
| cacactatca atttctgaaa taaaaacagc agacattcct gatactgatt tgtcctctgt | 780 |
| tggagttgta agctatggtg atttcgccat agaagtgata gatcctgttt cagattacct | 840 |
| tgaactaatg gagaatgtgt tgacttcca acttatcaag gatttgcttt ctcggcctga | 900 |
| tttcaggttc atatttgatg caatgcatgc aattactggt gcgtatgccg gacccatttt | 960 |
| tgttgagaaa cttggagctg atccggactg catattaaat gggggtgcctc ttgaagattt | 1020 |
| tggaaatggc catccagatc caaatctaac ttacgctaag gagcttgttt ttactatgtt | 1080 |
| tggaacccat gcacctgact ttggtgcagc aagtgatggt gatggtgatc ggaacatgat | 1140 |
| tcttgggaaa aggttcttta ttaccccatc agactctgtt gcaataattg cagccaatgc | 1200 |
| acagacagca attccttatt ccagtttggg tacaaaagga ctcgcgagat caatgccaac | 1260 |
| cagtggtgct cttgatcgtg ttgccgagaa attgaatgtt ccattctttg aggttccaac | 1320 |
| aggctgaaa ttttttggca acctaatgga tgcaggaaaa ttgtctattt gtggagagga | 1380 |
| aagttttggg actggatctg atcacatcag agagaaggat ggcatctggg ctgttctggc | 1440 |
| ttggcttcc atacttgcac accggaacaa ggataagaag gtcggagaga gattagtgtc | 1500 |
| agttgaagat attgctatgg agcactggaa aacctatggc aggaatttct tttctagata | 1560 |
| cgattatgag gcgtgtgaat cacacagtgc aaaccagatg atggatcacc ttagagatgt | 1620 |
| tatggcaaat agcaagcctg agagaaata cggaaattac ccctccaat tgctgatga | 1680 |
| tttcagctat actgatcctg tagacggtag tacggtatca aaacaaggac ttcgatttgt | 1740 |
| tttcactgat ggatctagga ttatcttccg gctttcggga accggatctg ctggagctac | 1800 |
| tatccgcctc tacatagaac aatttgaatc tgatatctcg aagcatagtc tcgatgctca | 1860 |
| aacagctttg aagcctttaa tagacctggc tttgtctgtt tcgaagctca aggacttcac | 1920 |
| aggaagagag aaacctactg tcataacata ggccctgttt gtttcggctt ttggcagctt | 1980 |
| ctggccacca aaagctactg cgtactgtca acgctcagc ttttcagcca gcttctataa | 2040 |

-continued

```
aattcgttgg gggcaaaaac catctaaaat caaataaaca cataatcggt tgagtcgttg      2100
taatagtagg aattcatcac tttctagatc ctgagcctta tgaacaactt tatcttccta      2160
cacacataat cgtaatgata ctcagattct cccacagcca gattctcccc acagccagat      2220
tttcagaaaa gttggtcaga aaaaagctga accaaacagc cccataatat ttagatgttg      2280
ttgtcctcgg ccataccaac tgagcagcat gggccaagaa ttgaactgat ggaaaatatg      2340
tatcattagg acaaattccg ccagaataag ttgttcctcg gaaaaaaaaa aaaaaaaaa       2400 g                                                                      2401
```

<210> SEQ ID NO 17
<211> LENGTH: 4974
<212> TYPE: DNA
<213> ORGANISM: synthetic construct
<220> FEATURE:
<221> NAME/KEY: unsure
<222> LOCATION: (3951)
<223> OTHER INFORMATION: n = A, C, G, or T

<400> SEQUENCE: 17

```
ggccgccgac tcgacgatga gcgagatgac cagctccggc cgcgacacaa gtgtgagagt        60
actaaataaa tgctttggtt gtacgaaatc attacactaa ataaataat caaagcttat        120 atatgccttc cgctaaggcc gaatgcaaag aaattggttc tttctcgtta tcttttgcca       180
cttttactag tacgtattaa ttactactta atcatctttg tttacggctc attatatccg       240
tcgacggcgc gcccgatcat ccggatatag ttcctccttt cagcaaaaaa cccctcaaga       300
cccgtttaga ggccccaagg ggttatgcta gttattgctc agcggtggca gcagccaact       360
cagcttcctt tcgggctttg ttagcagccg gatcgatcca agctgtacct cactattcct       420
ttgccctcgg acgagtgctg gggcgtcggt ttccactatc ggcgagtact tctacacagc       480
catcggtcca gacggccgcg cttctgcggg cgatttgtgt acgcccgaca gtcccggctc       540
cggatcggac gattgcgtcg catcgaccct gcgcccaagc tgcatcatcg aaattgccgt       600
caaccaagct ctgatagagt tggtcaagac caatgcggag catatacgcc cggagccgcg       660
gcgatcctgc aagctccgga tgcctccgct cgaagtagcg cgtctgctgc tccatacaag       720
ccaaccacgg cctccagaag aagatgttgg cgacctcgta ttgggaatcc ccgaacatcg       780
cctcgctcca gtcaatgacc gctgttatgc ggccattgtc cgtcaggaca ttgttggagc       840
cgaaatccgc gtgcacgagg tgccggactt cggggcagtc ctcggcccaa agcatcagct       900
catcgagagc ctgcgcgacg gacgcactga cggtgtcgtc catcacagtt tgccagtgat       960
acacatgggg atcagcaatc gcgcatatga atcacgccca tgtagtgtat tgaccgattc      1020
cttgcggtcc gaatgggccg aacccgctcg tctggctaag atcggccgca gcgatcgcat      1080
ccatagcctc cgcgaccggc tgcagaacag cgggcagttc ggtttcaggc aggtcttgca      1140
acgtgacacc ctgtgcacgg cgggagatgc aataggtcag gctctcgctg aattccccaa      1200
tgtcaagcac ttccggaatc gggagcgcgg ccgatgcaaa gtgccgataa acataacgat      1260
ctttgtagaa accatcggcg cagctattta cccgcaggac atatccacgc cctcctacat      1320
cgaagctgaa agcacgagat tcttcgccct ccgagagctg catcaggtcg gagacgctgt      1380
cgaacttttc gatcagaaac ttctcgacag acgtcgcggt gagttcaggc ttttccatgg      1440
gtatatctcc ttcttaaagt taaacaaaat tatttctaga gggaaaccgt tgtggtctcc      1500
ctatagtgag tcgtattaat ttcgcgggat cgagatctga tcaacctgca ttaatgaatc      1560
ggccaacgcg cggggagagg cggtttgcgt attgggcgct cttccgcttc ctcgctcact      1620
```

```
gactcgctgc gctcggtcgt tcggctgcgg cgagcggtat cagctcactc aaaggcggta   1680
atacggttat ccacagaatc aggggataac gcaggaaaga acatgtgagc aaaaggccag   1740
caaaaggcca ggaaccgtaa aaaggccgcg ttgctggcgt ttttccatag gctccgcccc   1800
cctgacgagc atcacaaaaa tcgacgctca agtcagaggt ggcgaaaccc gacaggacta   1860
taaagatacc aggcgtttcc ccctggaagc tccctcgtgc gctctcctgt tccgaccctg   1920
ccgcttaccg gatacctgtc cgcctttctc ccttcgggaa gcgtggcgct ttctcaatgc   1980
tcacgctgta ggtatctcag ttcggtgtag gtcgttcgct ccaagctggg ctgtgtgcac   2040
gaaccccccg ttcagcccga ccgctgcgcc ttatccggta actatcgtct tgagtccaac   2100
ccggtaagac acgacttatc gccactggca gcagccactg gtaacaggat tagcagagcg   2160
aggtatgtag gcggtgctac agagttcttg aagtggtggc ctaactacgg ctacactaga   2220
aggacagtat ttggtatctg cgctctgctg aagccagtta ccttcggaaa aagagttggt   2280
agctcttgat ccggcaaaca aaccaccgct ggtagcggtg gtttttttgt ttgcaagcag   2340
cagattacgc gcagaaaaaa aggatctcaa gaagatcctt tgatcttttc tacggggtct   2400
gacgctcagt ggaacgaaaa ctcacgttaa gggattttgg tcatgacatt aacctataaa   2460
aataggcgta tcacgaggcc ctttcgtctc gcgcgtttcg gtgatgacgg tgaaaacctc   2520
tgacacatgc agctcccgga gacggtcaca gcttgtctgt aagcggatgc cgggagcaga   2580
caagcccgtc agggcgcgtc agcgggtgtt ggcgggtgtc ggggctggct taactatgcg   2640
gcatcagagc agattgtact gagagtgcac catatggaca tattgtcgtt agaacgcggc   2700
tacaattaat acataacctt atgtatcata cacatacgat ttaggtgaca ctatagaacg   2760
gcgcgccaag cttggatcct cgaagagaag ggttaataac acattttta acatttttaa   2820
cacaaatttt agttatttaa aaatttatta aaaaatttaa aataagaaga ggaactcttt   2880
aaataaatct aacttacaaa atttatgatt tttaataagt tttcaccaat aaaaaatgtc   2940
ataaaaatat gttaaaaagt atattatcaa tattctcttt atgataaata aaaagaaaaa   3000
aaaaataaaa gttaagtgaa atgagattga agtgactttt aggtgtgtat aaatatatca   3060
accccgccaa caatttattt aatccaaata tattgaagta tattattcca tagcctttat   3120
ttatttatat atttattata taaaagcttt atttgttcta ggttgttcat gaaatatttt   3180
tttggtttta tctccgttgt aagaaaatca tgtgctttgt gtcgccactc actattgcag   3240
cttttttcatg cattggtcag attgacggtt gattgtattt tgttttttta tggttttgtg   3300
ttatgactta agtcttcatc tctttatctc ttcatcaggt ttgatggtta cctaatatgg   3360
tccatgggta catgcatggt taaattaggt ggccaacttt gttgtgaacg atagaatttt   3420
ttttatatta agtaaactat ttttatatta tgaaataata ataaaaaaaa tattttatca   3480
ttattaacaa aatcatatta gttaatttgt taactctata ataaaagaaa tactgtaaca   3540
ttcacattac atggtaacat cttttccaccc tttcatttgt tttttgtttg atgacttttt   3600
ttcttgttta aatttatttc ccttcttttta aatttggaat acattatcat catatataaa   3660
ctaaaatact aaaacagga ttacacaaat gataaaataat aacacaaata tttataaatc   3720
tagctgcaat atatttaaac tagctatatc gatattgtaa aataaaacta gctgcattga   3780
tactgataaa aaaatatcat gtgctttctg gactgatgat gcagtatact tttgacattg   3840
cctttatttt attttcaga aaagctttct tagttctggg ttcttcatta tttgtttccc   3900
atctccattg tgaattgaat catttgcttc gtgtcacaaa tacaatttag ntaggtacat   3960
gcattggtca gattcacggt ttattatgtc atgacttaag ttcatggtag tacattacct   4020
```

```
gccacgcatg cattatattg gttagatttg ataggcaaat ttggttgtca acaatataaa    4080
tataaataat gttttatat tacgaaataa cagtgatcaa acaaacagt tttatcttta      4140 ttaacaagat tttgttttg tttgatgacg ttttttaatg tttacgcttt ccccttctt      4200 ttgaatttag aacactttat catcataaaa tcaaatacta aaaaattac atatttcata     4260 aataataaca caatatttt taaaaaatct gaaataataa tgaacaatat tacatattat     4320
cacgaaaatt cattaataaa aatattatat aaataaatg taatagtagt tatatgtagg     4380 aaaaagtac tgcacgcata atatatacaa aaagattaaa atgaactatt ataaataata    4440
acactaaatt aatggtgaat catatcaaaa taatgaaaaa gtaaataaaa tttgtaatta    4500
acttctatat gtattacaca cacaaataat aaataatagt aaaaaaatt atgataaata    4560 tttaccatct cataagatat ttaaaataat gataaaaata tagattattt tttatgcaac   4620
tagctagcca aaaagagaac acgggtatat ataaaaagag tacctttaaa ttctactgta   4680
cttcctttat tcctgacgtt tttatatcaa gtggacatac gtgaagattt taattatcag  4740
tctaaatatt tcattagcac ttaatacttt tctgttttat tcctatccta taagtagtcc   4800
cgattctccc aacattgctt attcacacaa ctaactaaga aagtcttcca tagcccccca   4860
agcggccgga gctggtcatc tcgctcatcg tcgagtcggc ggccggagct ggtcatctcg   4920
ctcatcgtcg agtcggcggc cgccgactcg acgatgagcg agatgaccag ctcc          4974

<210> SEQ ID NO 18
<211> LENGTH: 34
<212> TYPE: DNA
<213> ORGANISM: Artificial Sequence
<220> FEATURE:
<223> OTHER INFORMATION: Synthetic DNA Linker

<400> SEQUENCE: 18
ggcgcgccaa gcttggatcc gtcgacggcg cgcc                                 34

<210> SEQ ID NO 19
<211> LENGTH: 80
<212> TYPE: DNA
<213> ORGANISM: Artificial Sequence
<220> FEATURE:
<223> OTHER INFORMATION: Synthetic Complementary Region of pKS106 and
      pKS124

<400> SEQUENCE: 19
cggccggagc tggtcatctc gctcatcgtc gagtcggcgg ccgccgactc gacgatgagc     60
gagatgacca gctccggccg                                                 80

<210> SEQ ID NO 20
<211> LENGTH: 154
<212> TYPE: DNA
<213> ORGANISM: Artificial Sequence
<220> FEATURE:
<223> OTHER INFORMATION: Synthetic Complementary Region of pKS133

<400> SEQUENCE: 20
cggccggagc tggtcatctc gctcatcgtc gagtcggcgg ccggagctgg tcatctcgct     60
catcgtcgag tcggcggccg ccgactcgac gatgagcgag atgaccagct ccggccgccg    120
actcgacgat gagcgagatg accagctccg gccg                                154

<210> SEQ ID NO 21
<211> LENGTH: 92
<212> TYPE: DNA
<213> ORGANISM: Artificial Sequence
```

```
<220> FEATURE:
<223> OTHER INFORMATION: Synthetic PCR primer

<400> SEQUENCE: 21
gaattccggc cggagctggt catctcgctc atcgtcgagt cggcggccgc cgactcgacg      60
atgagcgaga tgaccagctc cggccggaat tc                                   92

<210> SEQ ID NO 22
<211> LENGTH: 15
<212> TYPE: DNA
<213> ORGANISM: Artificial Sequence
<220> FEATURE:
<223> OTHER INFORMATION: Synthetic PCR primer

<400> SEQUENCE: 22
gaattccggc cggag                                                      15
```